(12) United States Patent
Bowen et al.

(10) Patent No.: US 8,629,116 B2
(45) Date of Patent: Jan. 14, 2014

(54) METHOD FOR INDUCING A TRIF-BIAS

(75) Inventors: William S. Bowen, Hamilton, MT (US); Jay T. Evans, Hamilton, MT (US); Melinda M. Hutton, Hamilton, MT (US); David A. Johnson, Hamilton, MT (US); Laurie A. Minns, Shoreline, WA (US)

(73) Assignee: GlaxoSmithKline Biologicals S.A., Rixensart (BE)

( * ) Notice: Subject to any disclaimer, the term of this patent is extended or adjusted under 35 U.S.C. 154(b) by 12 days.

(21) Appl. No.: 13/140,930

(22) PCT Filed: Dec. 23, 2009

(86) PCT No.: PCT/US2009/069465
§ 371 (c)(1),
(2), (4) Date: Jun. 20, 2011

(87) PCT Pub. No.: WO2010/075545
PCT Pub. Date: Jul. 1, 2010

(65) Prior Publication Data
US 2011/0257113 A1    Oct. 20, 2011

Related U.S. Application Data

(60) Provisional application No. 61/140,226, filed on Dec. 23, 2008.

(51) Int. Cl.
*A61K 31/7032*    (2006.01)

(52) U.S. Cl.
USPC ............................................. 514/25

(58) Field of Classification Search
USPC ............................................. 514/25
See application file for complete search history.

(56) References Cited

U.S. PATENT DOCUMENTS

| | | | |
|---|---|---|---|
| 6,113,918 A | 9/2000 | Johnson et al. | |
| 7,902,159 B2 * | 3/2011 | Persing et al. | 514/25 |
| 2007/0225254 A1 * | 9/2007 | Persing et al. | 514/62 |
| 2011/0178034 A1 * | 7/2011 | Persing et al. | 514/25 |

FOREIGN PATENT DOCUMENTS

WO    2006016997    2/2006

OTHER PUBLICATIONS

Mata-Haro et al. The vaccine adjuvant monophosphoryl lipid A as a TRIF-biased agonist of TLR4. Science 316:1628-1631, Jun. 2007.*
Zughaier et al. Differential induction of the Toll-like receptor 4-MyD88-dependent and -independent signaling pathways by endotoxins. Infect Immunity 73:2940-2950, May 2005.*

* cited by examiner

*Primary Examiner* — Wu-Cheng Winston Shen
*Assistant Examiner* — Yih-Horng Shiao
(74) *Attorney, Agent, or Firm* — Michael M. Conger

(57) ABSTRACT

The use of a selected aminoalkyl glusoaminide 4-phosphate (AGP) CRX-547 to induce a TRIF biased response in a human system, which results in reduced levels of MyD88-dependent cytokines relative to the MyD88-dependent cytokines induced by its diastereomer AGP CRX-527.

1 Claim, 35 Drawing Sheets

L-Seryl Isomer | D-Seryl Isomer
CRX-527
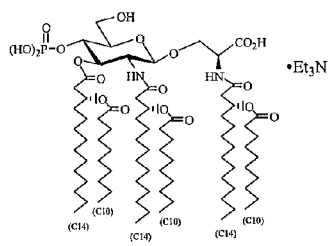
1a
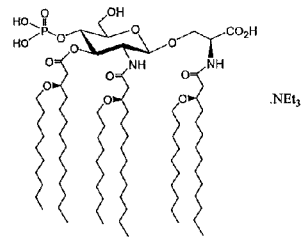
CRX-547
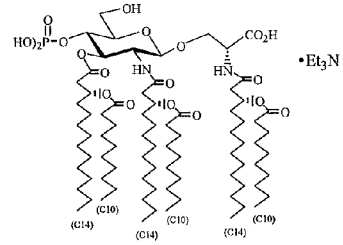
1b
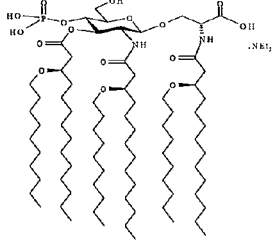
Figure 1.   Aminoalkyl glucosaminide 4-phosphates with ester-linked fatty acyl chains, CRX-527 and CRX-547 1a/1b; Aminoalkyl glucosaminide 4-phosphates with ether-linked fatty acyl chains, compounds (L/D isomers) 1a/b.

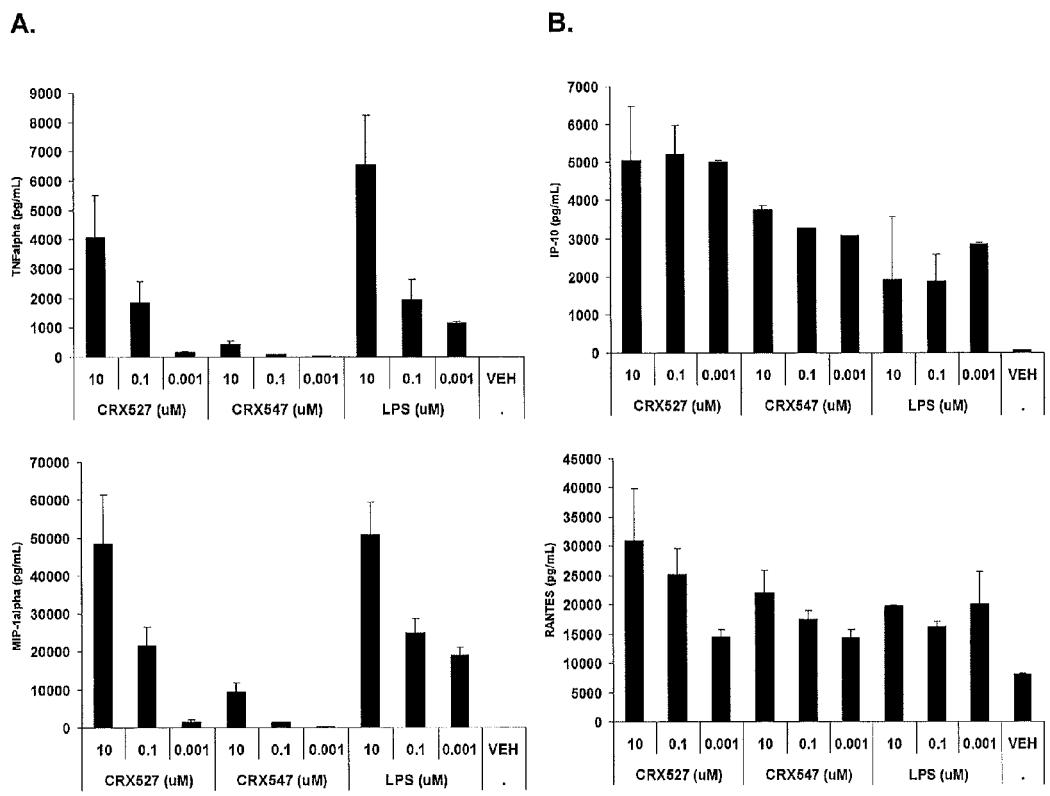
Figure 2. Comparison of the Lipid A mimetics, CRX-527 and CRX-547 with *S. minn.* Re595 LPS for induction of (A) MyD88-dependent and (B) TRIF-dependent cytokines and chemokines in human PBMCs.

A.
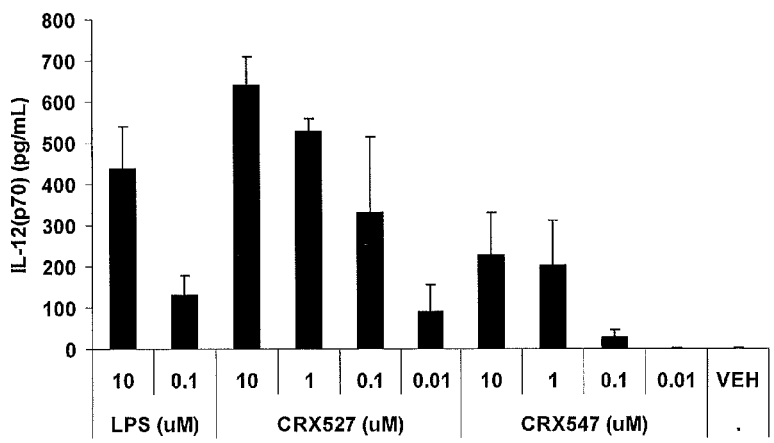
B.
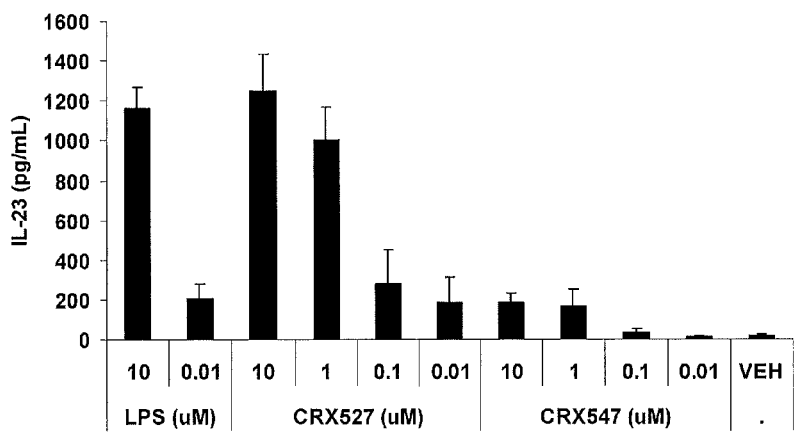
Figure 3. Induction of (A) IL-12p70 and (B) IL-23, by treatment of human monocyte-derived dendritic cells with *S. minn.* Re595 LPS, CRX-527 and CRX-547.

A.
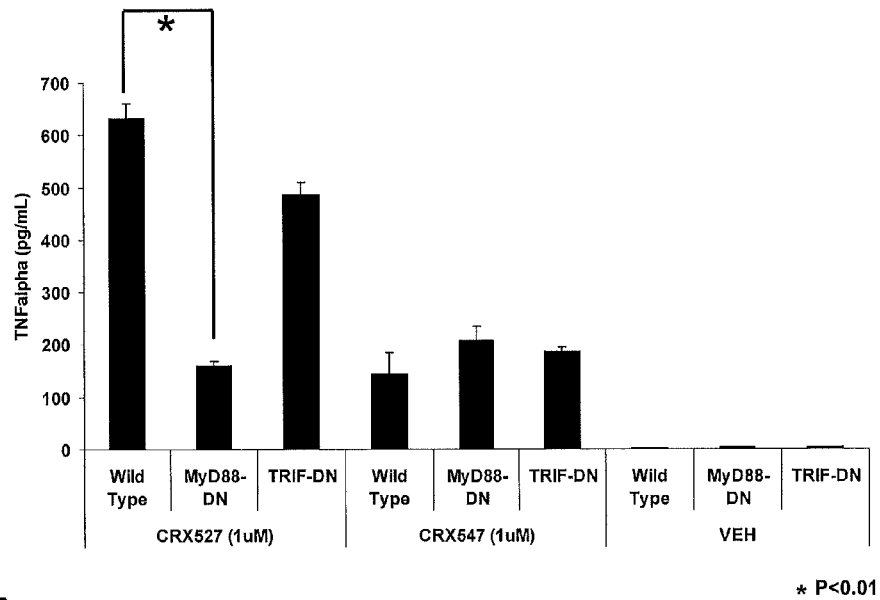
* P<0.01
B.
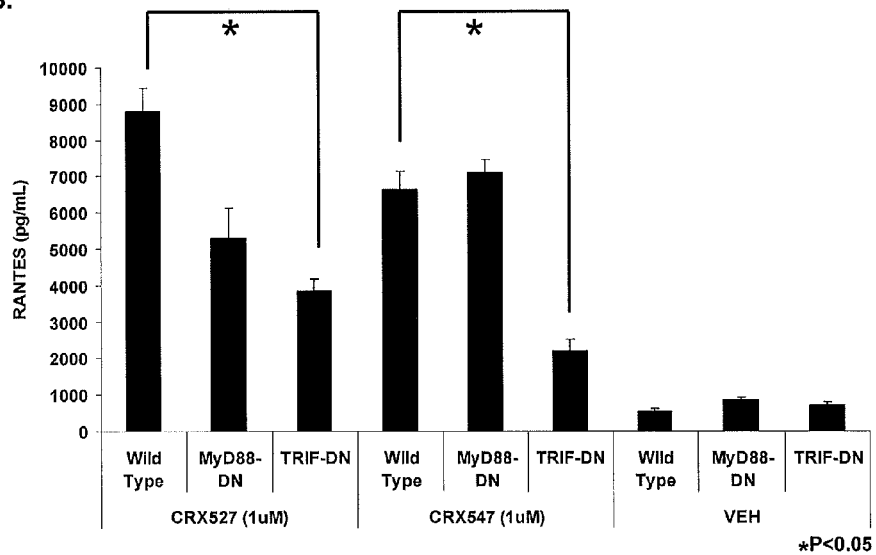
*P<0.05
Figure 4.  Inhibition of (A) MyD88- and (B) TRIF-dependent cytokine/chemokine induction in a human macrophages cell line by transfection of plasmids expressing dominant negative constructs of MyD88 (MyD88-DN) and TRIF (TRIF-DN).

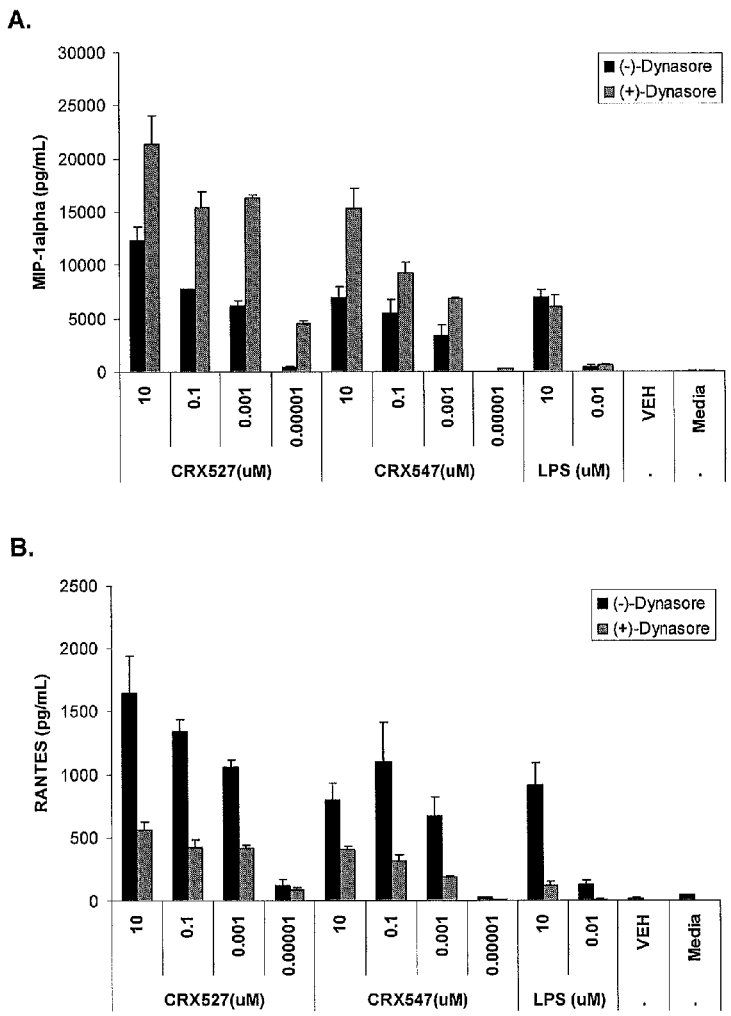
Figure 5. (A) MyD88-dependent (MIP-1α) and (B) TRIF-dependent (RANTES) cytokines/chemokines induced by CRX-527, CRX-547, and LPS in the presence of the endocytosis inhibitor, Dynasore.

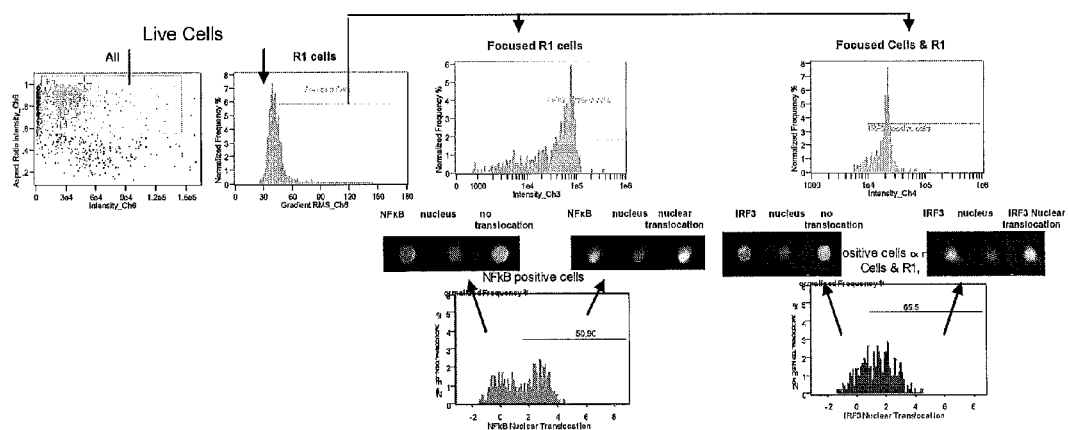
Figure 6. ImageStream gating strategy.

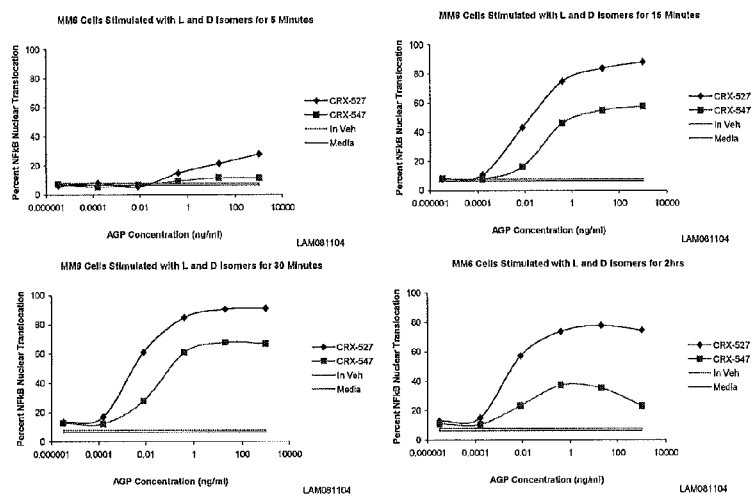
Figure 7. Human monocytic cells (MM6) were treated for 5, 15, 30, or 120 minutes with either CRX-527 or CRX-547 and nuclear translocation of NFκB was quantified as co-localization of the transcription factor with the nuclear dye (DRAK-5).

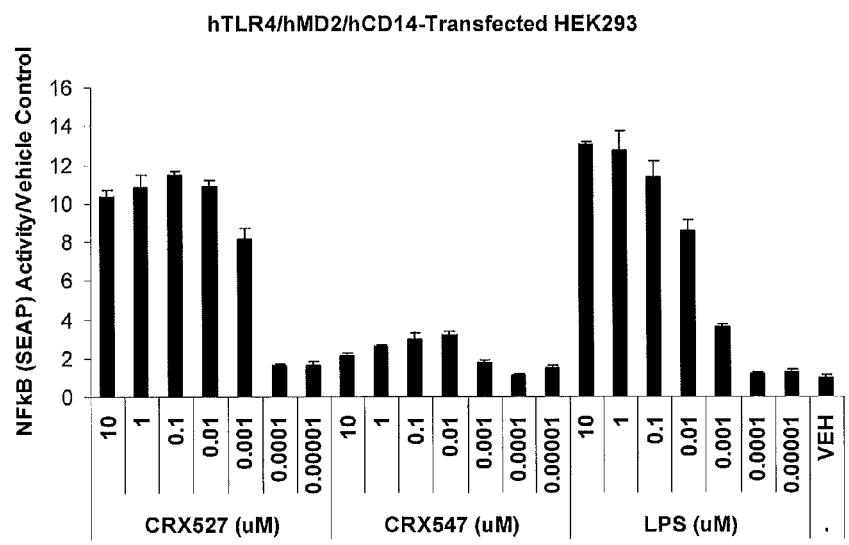
Figure 8. Comparison of NF-κB-inducible promoter activity when huTLR4/huMd-2/huCD14-transfected HEK293 cells are treated with *S. minn.* Re595 LPS, CRX-527, and CRX-547.

A.
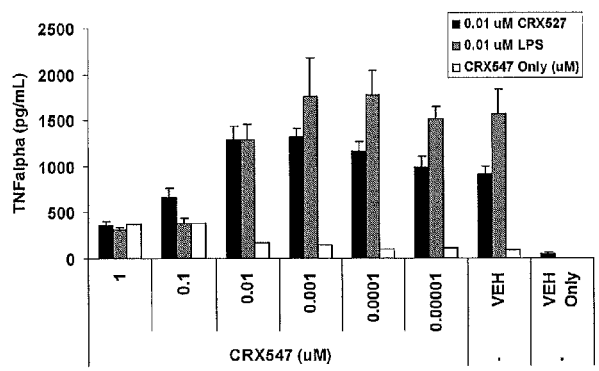
B.
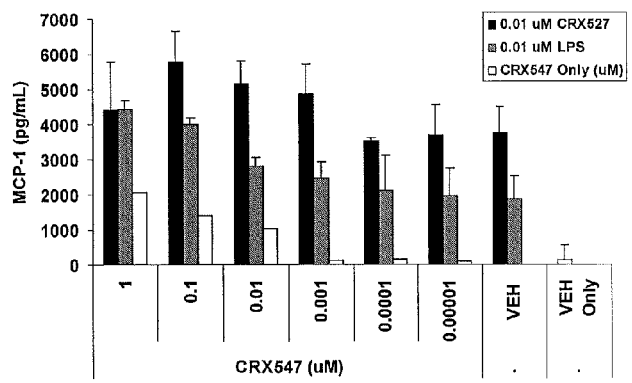
Figure 9. Inhibition of CRX-527 and LPS (A) MyD88-dependent and (B) TRIF-dependent cytokine/chemokine induction in the presence of increasing concentrations of CRX-547.

A.
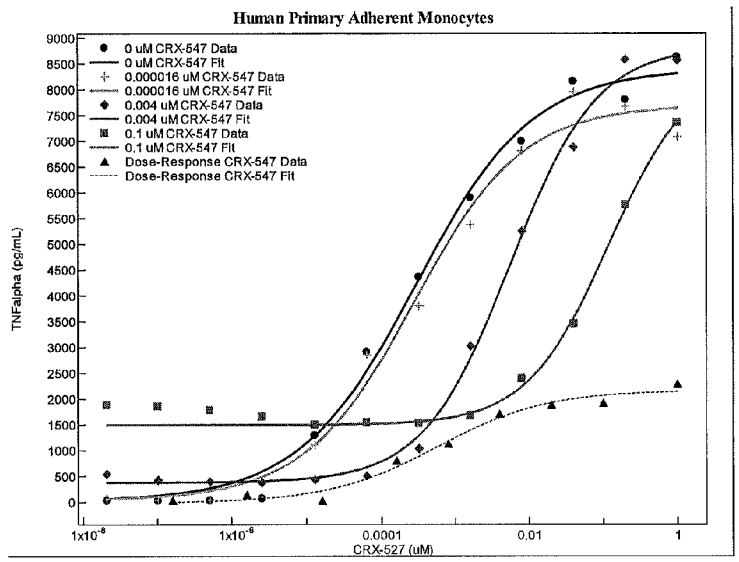
B.
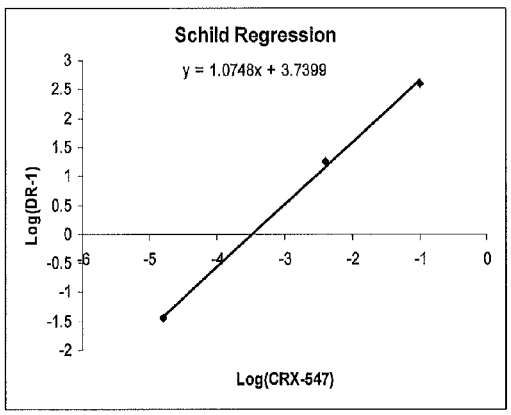
- CRX-547 $Kb_{app}$ = 0.33 nM
- CRX-547 $EC_{50}$ = 0.57 nM
- CRX-527 $EC_{50}$ = 0.29 nM
- %Efficacy$_{CRX-547}$ = 26%
Figure 10. (A) Inhibition of CRX-527-induced TNFα by the addition of increasing concentrations of CRX-547. (B) Schild regression analysis yields an estimate of CRX-547 affinity (0.33 nM) similar to the $EC_{50}$'s of both CRX-527 and CRX-547.

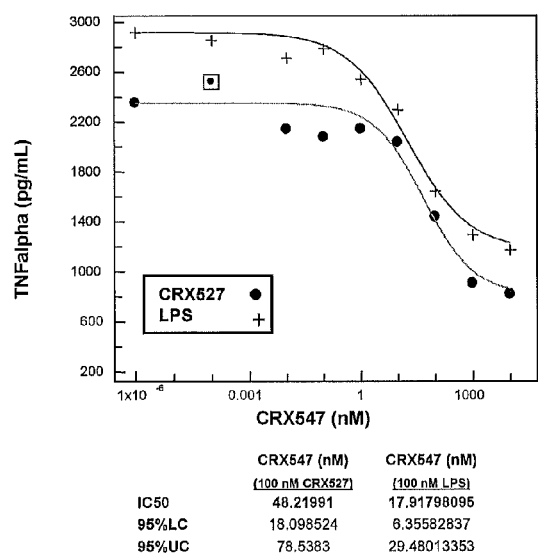
Figure 11. Inhibition of CRX527 and LPS MyD88-dependent (TNFα) cytokines induction in the presence of increasing concentrations of CRX547.

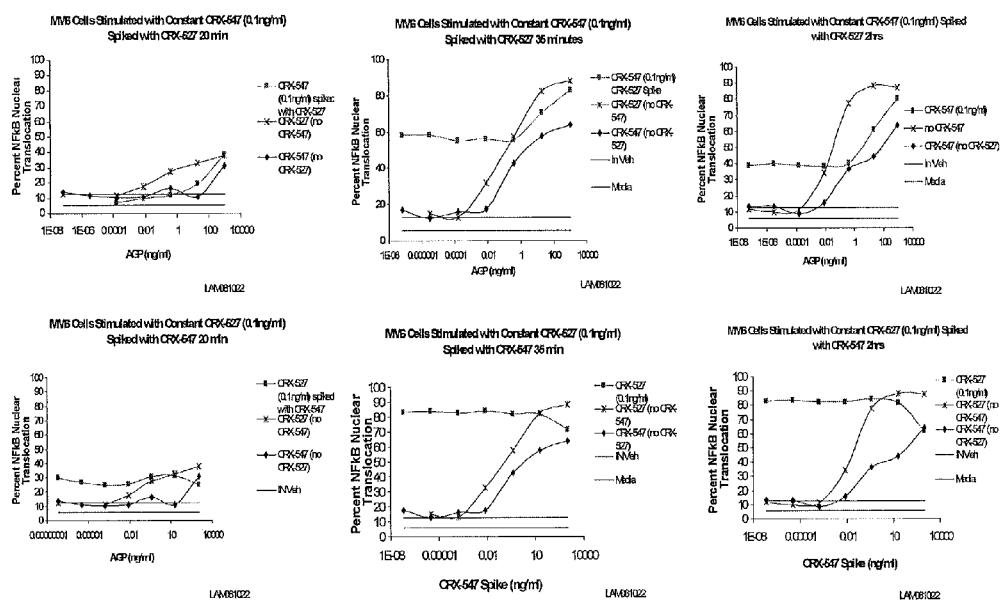
Figure 12. Inhibition of CRX527-induced NFκB nuclear translocation in the presence of increasing concentrations of CRX547.

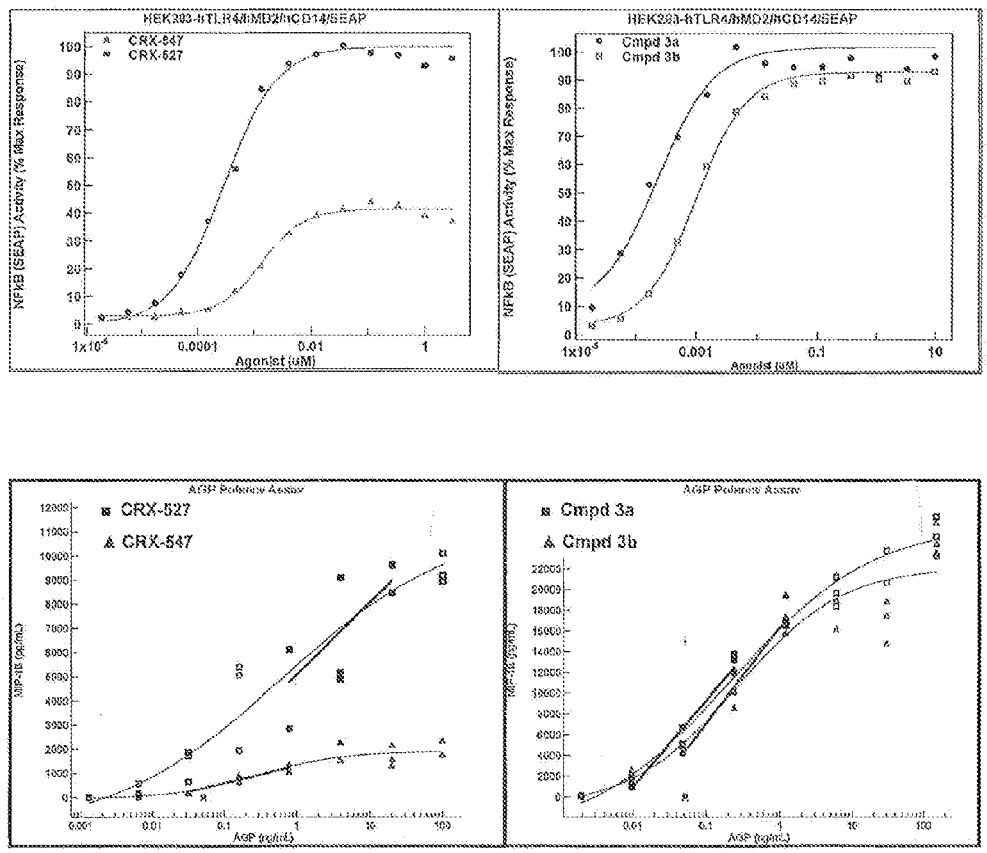
Figure 13. Effects of stability-enhancing modification of CRX-527/CRX-547 on signaling activity and chemokine induction. Comparison of (A) NFκB signaling in huTLR4/huMD-2/huCD14-transfected HEK293 cells and, (B) MyD88-dependent MIP-1β induction in human monocytic cells (MM6), by the L and D isomer pairs CRX-527/CRX-547 and 1a/1b.

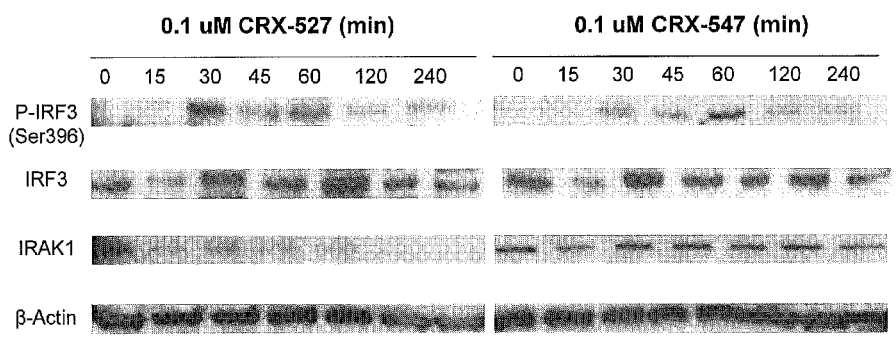
Figure 14. Western Blot analysis of human primary, PBMC-derived monocytes treated with CRX-527 showed similar kinetics and levels of activation of phosph-IRF3 downstream of TRIF and greater degradation of IRAK1 downstream of MyD88 than cells stimulated with CRX-547

A. MyD88 Signaling Proteins
B. TRIF Signaling proteins
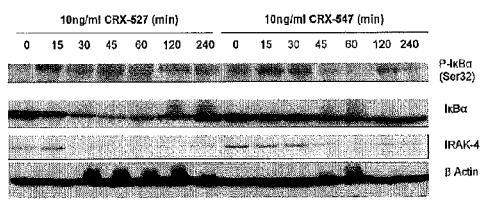
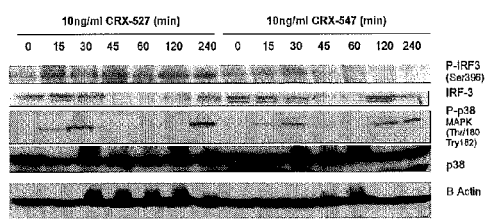
Figure 15.  Western Blot analysis of MM6 cells treated with CRX-527 showing greater degradation of IRAK4 downstream of MyD88 than cells stimulated with CRX-547

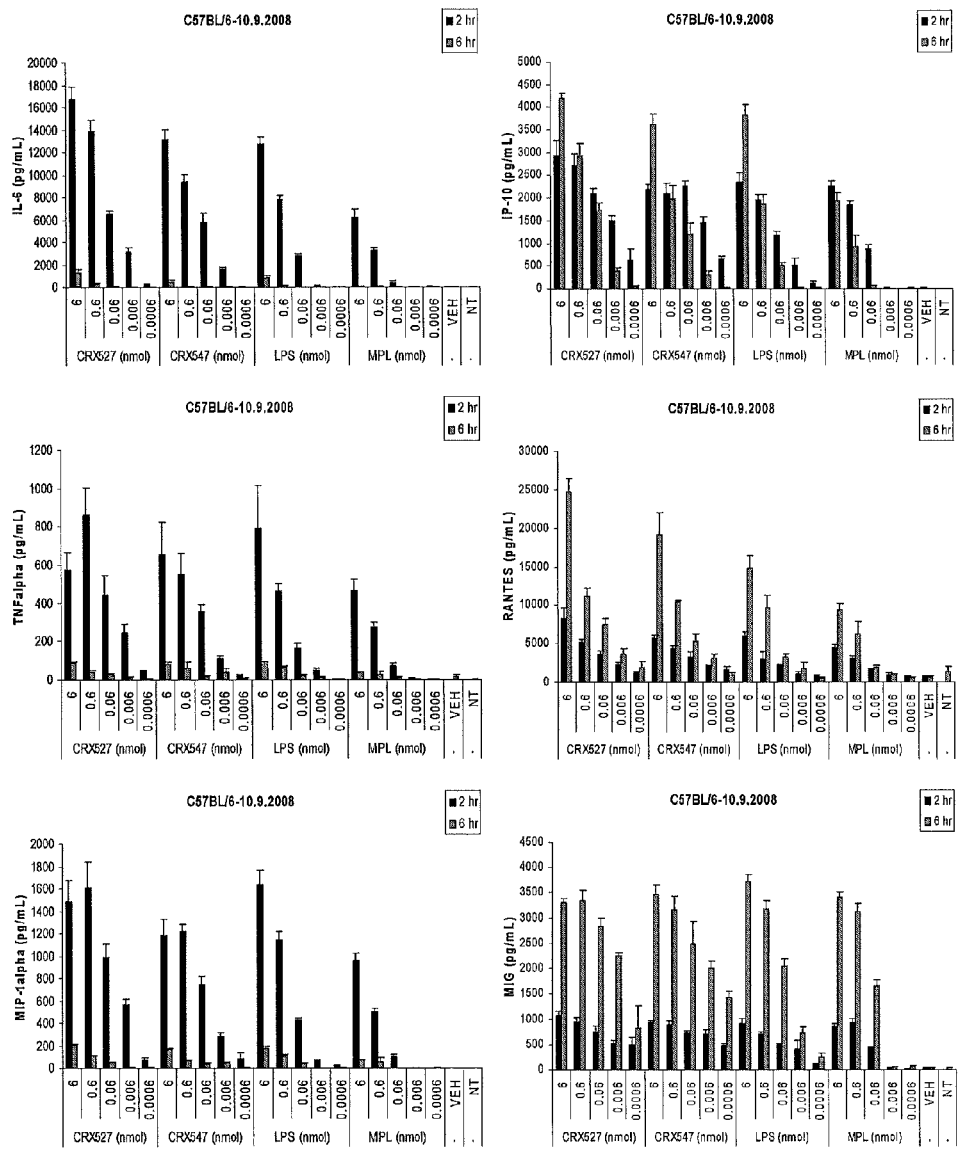
Figure 16. Induction of MyD88-dependent (MIP-1α, TNFα, IL-6) and TRIF-dependent (IP-10, RANTES, MIG) serum cytokines/ chemokines in C57BL/6 mice 2 and 6 hours after injection (IV) with CRX527, CRX547, LPS, and MPL.

A.
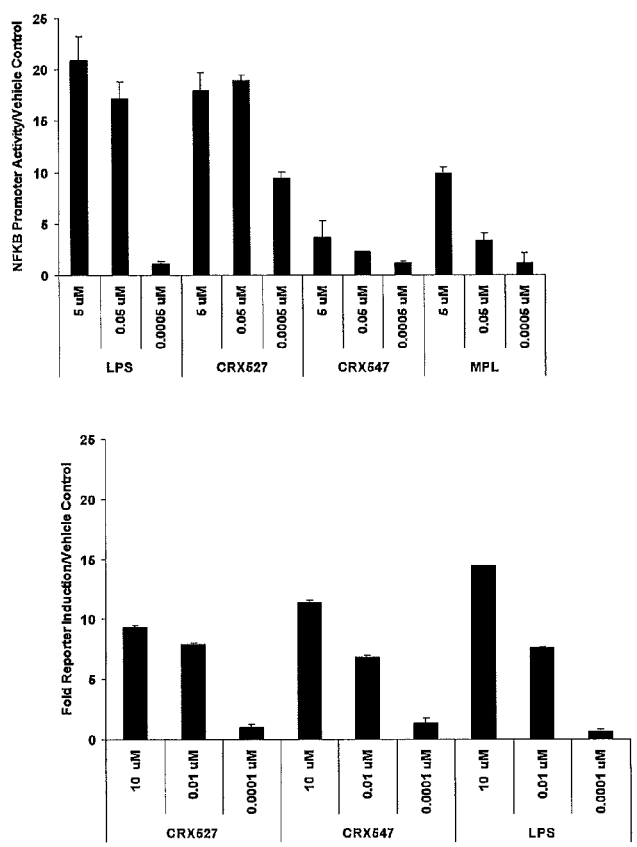
Figure 17. Induction of NFκB-dependent promoter activity by CRX-527, CRX-547, and LPS in HEK293 cells transfected with either human (top) and mouse (bottom) TLR4/MD-2/CD14

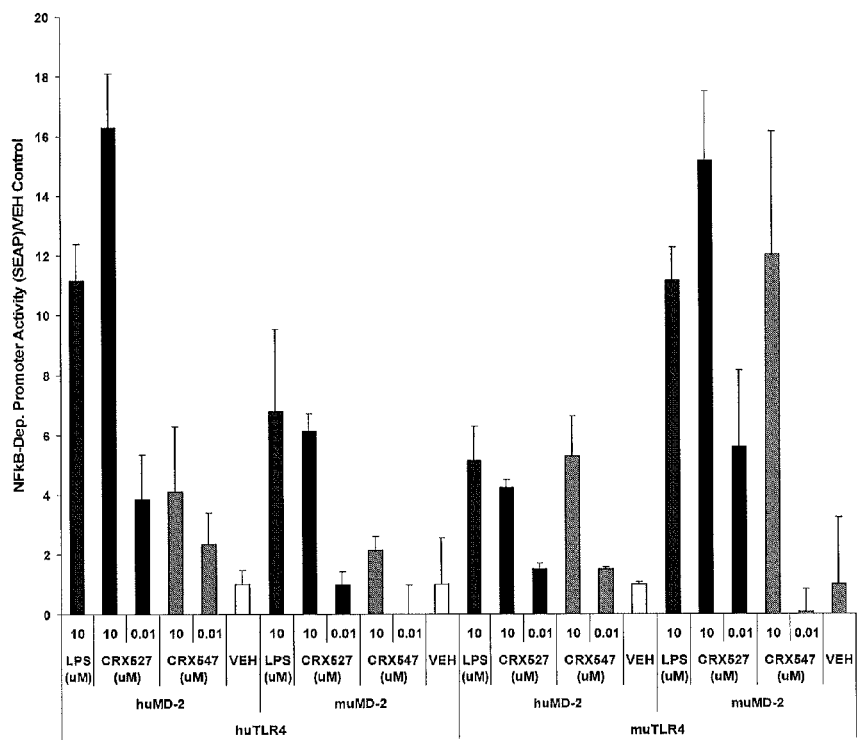
Figure 18. Induction of NFκB-dependent promoter activity in HEK293 cells transfected with either cognate human/mouse TLR4/MD-2 or chimeric combinations (huTLR4/muMD2 or muTLR4/huMD-2).

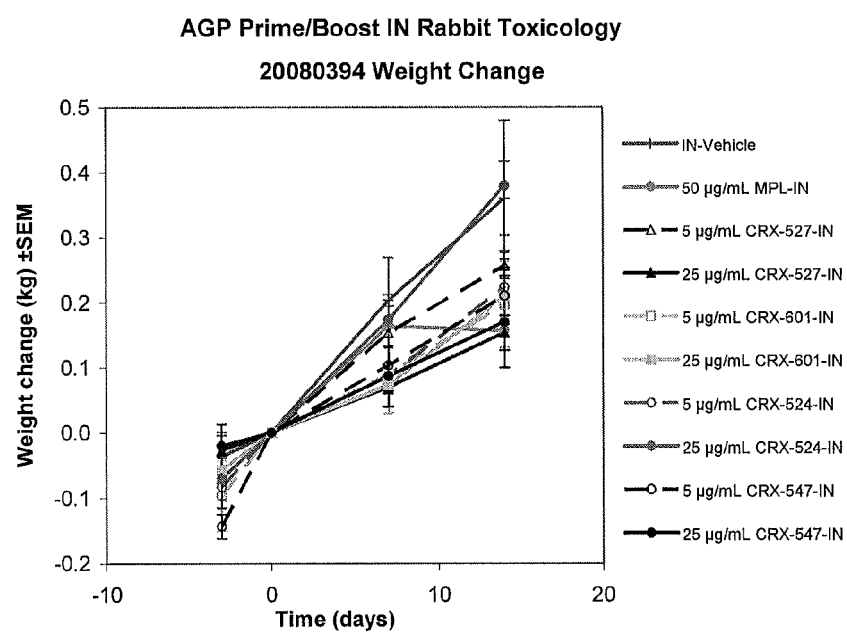
Figure 19. Weight change in rabbits treated with the indicated agonists.

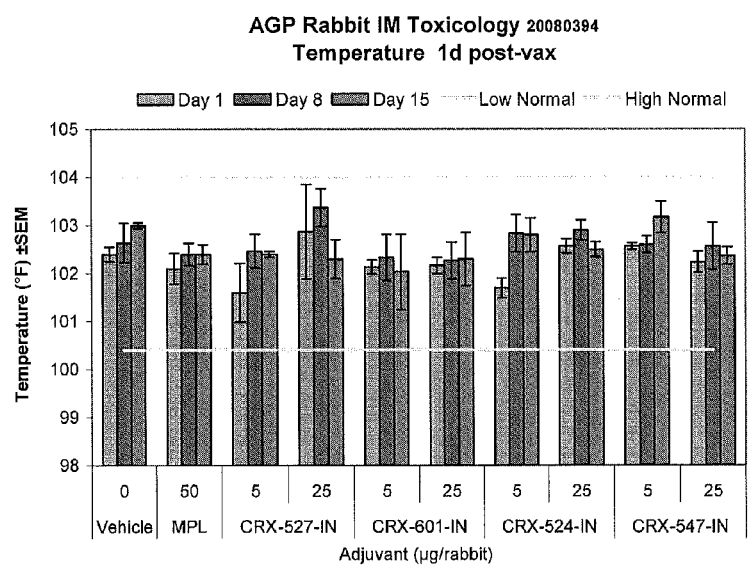
Figure 20. Post-vaccination temperature in rabbits treated with the indicated agonist.

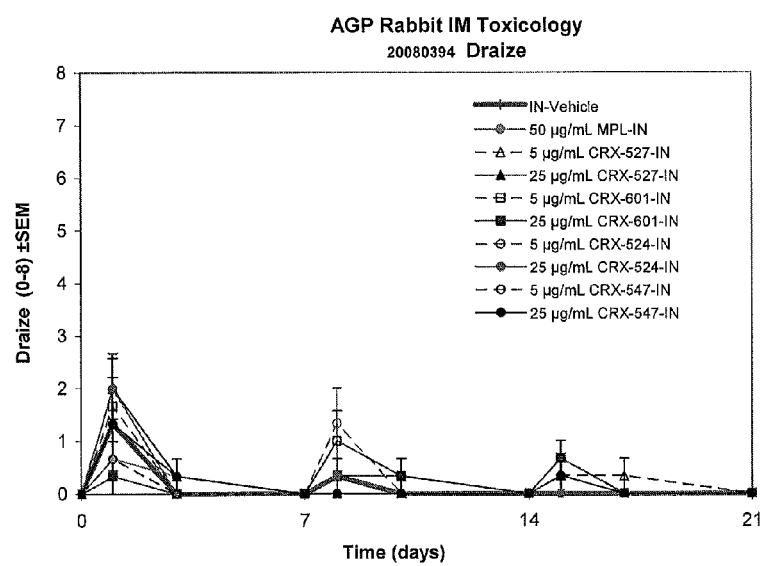
Figure 21. Injection site reactivity by Draize in rabbits treated with indicated agonists.

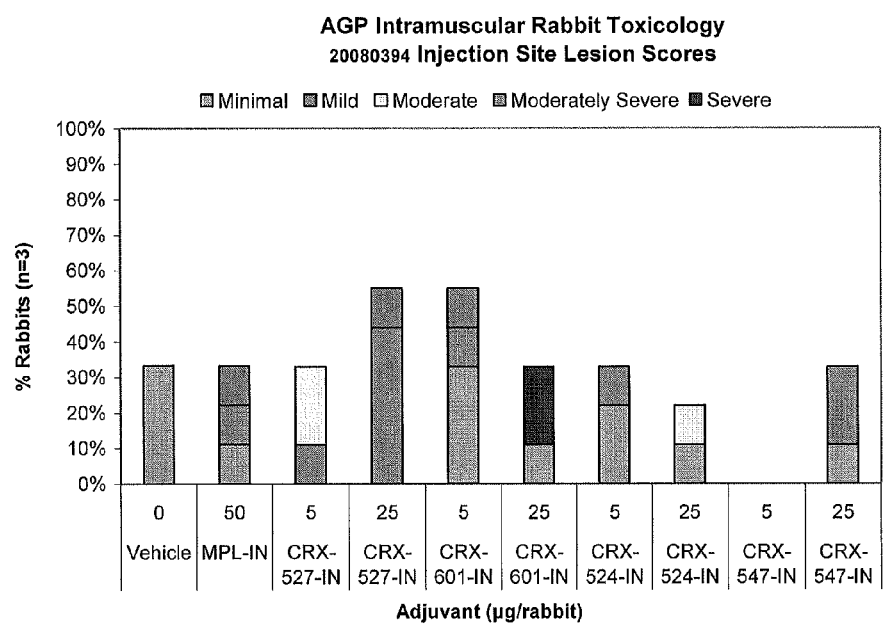
Figure 22. Injection site histopathology in rabbits treated with indicated agonists

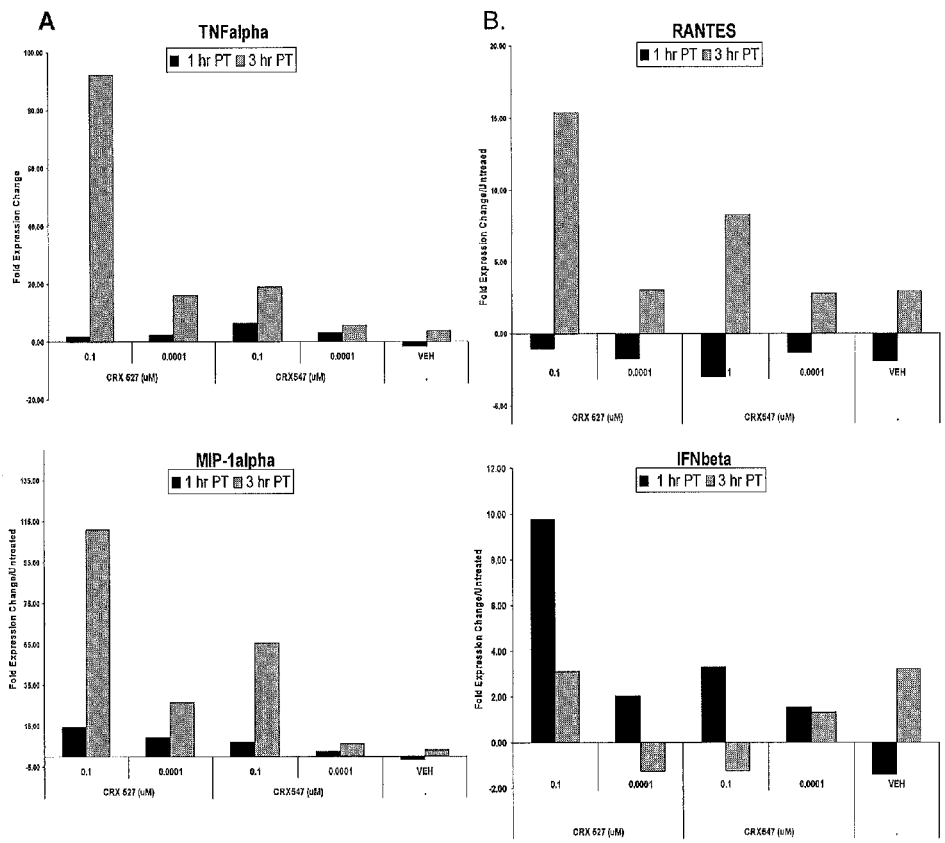
Figure 23. Induction of (A) MyD88-dependent, and (B) TRIF-dependent cytokine/chemokine gene expression in human PBMC-derived monocytes after treatment with 0.01 uM CRX-527 or CRX-547

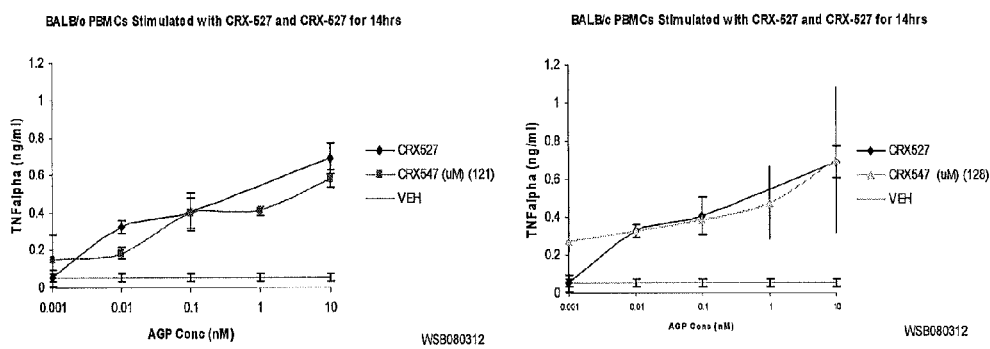
Figure 24. PBMCs from BALB/c Mice tested with CRX-547 (two lots) and CRX-527 (experiment performed once).

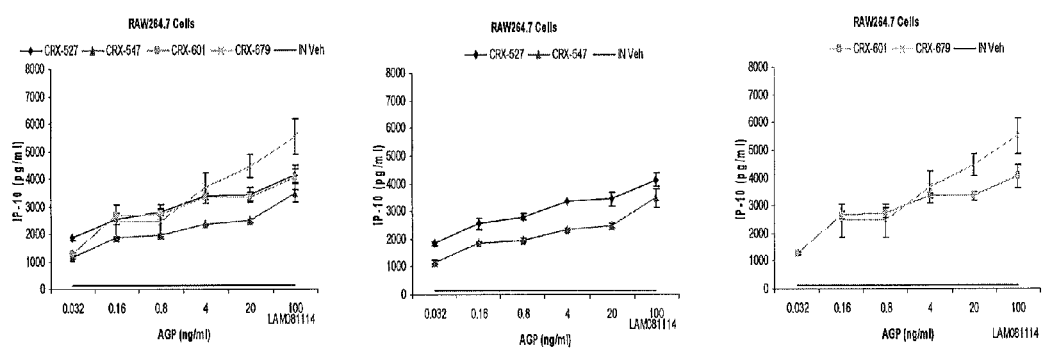
Figure 25. Induction of TRIF-dependent (IP-10) by CRX-527, CRX-547, Compound 1a and 1b

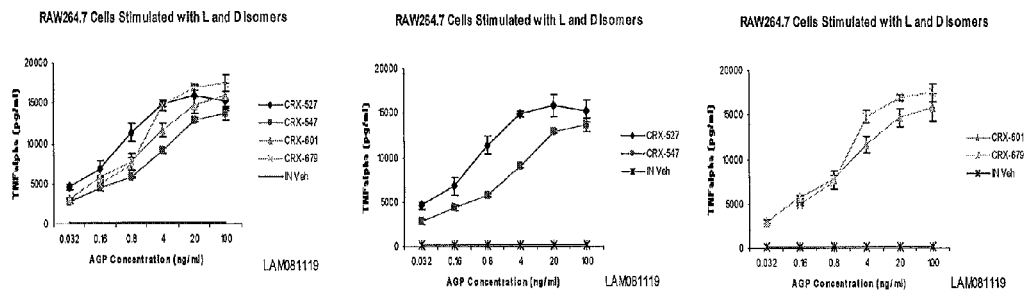
Figure 26. Induction of MyD88-dependent (TNFα) cytokine/chemokine by CRX-527, CRX-547, compound 1a and 1b.

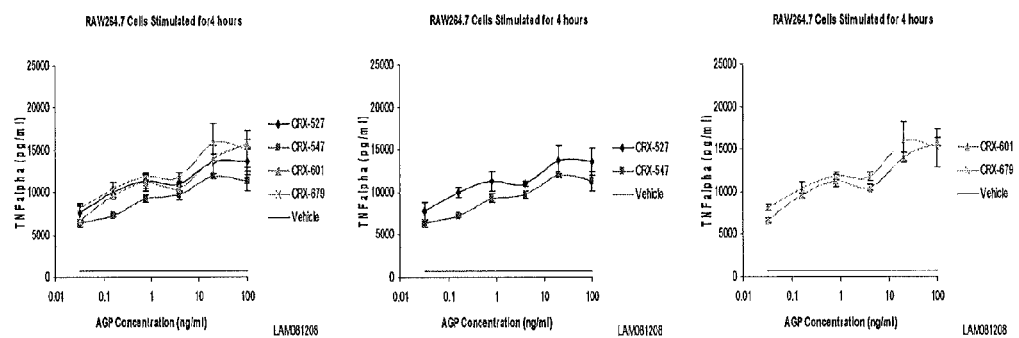
Figure 27. TNFα levels after four hours of stimulation with AGPs and their D isomers.

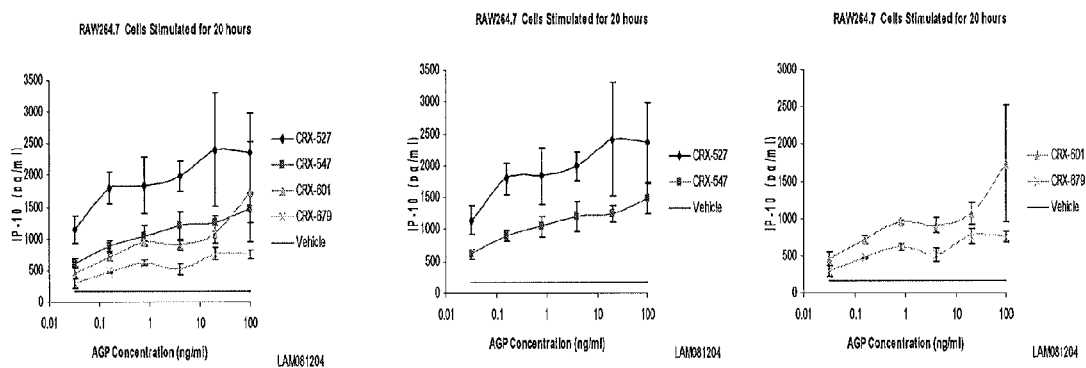
Figure 28. IP-10 levels after four hours of stimulation with AGPs and their D isomers.

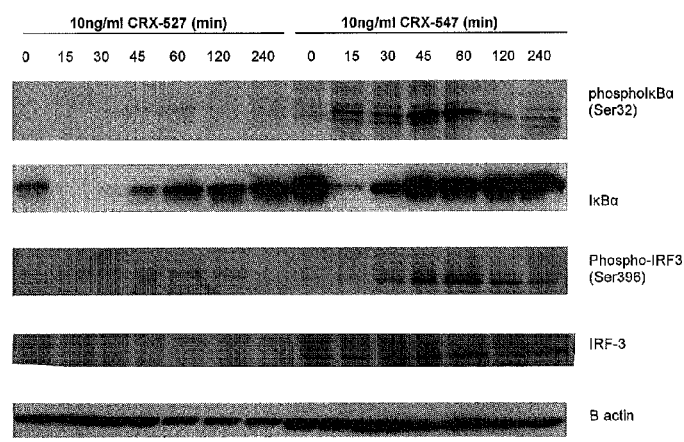
Figure 29. Western Blot analysis of Signaling Proteins after CRX-547 and CRX-527 stimulation in RAW264.7 Cells

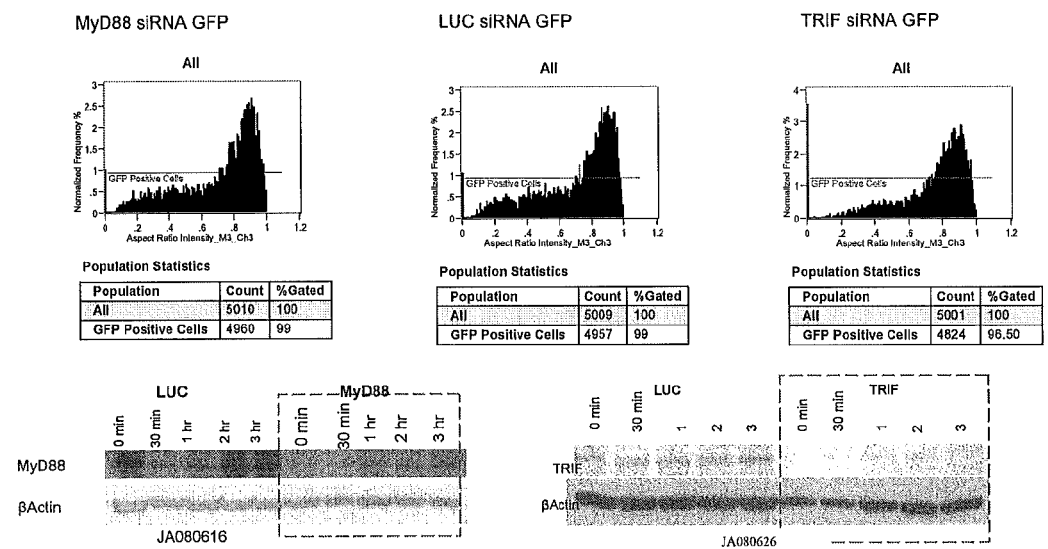
Figure 30.   Stably-transfected RAW264.7 Cells

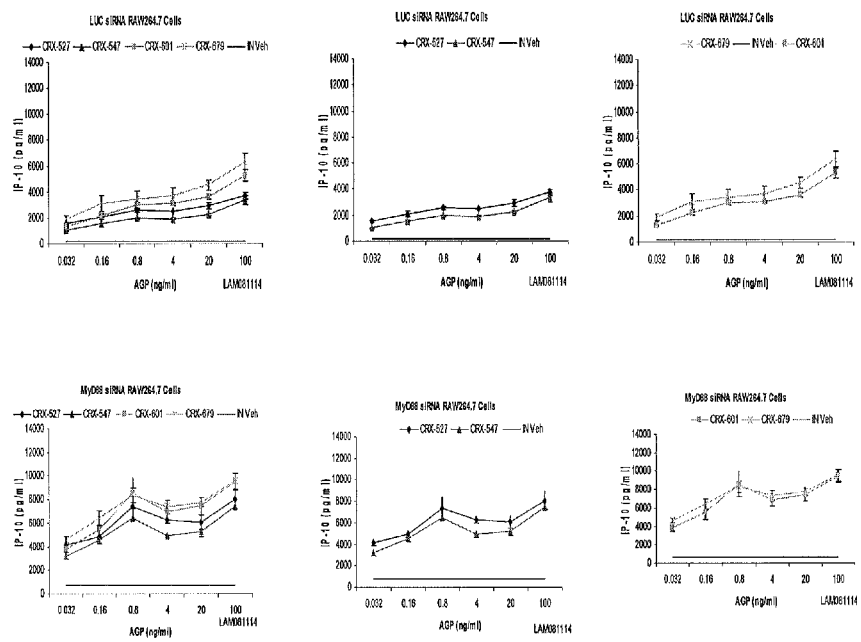
Figure 31. IP-10 Production after 20 hours of stimulation with L and D isomers (siRNA cell lines compared with the irrelevant control in each experiment).

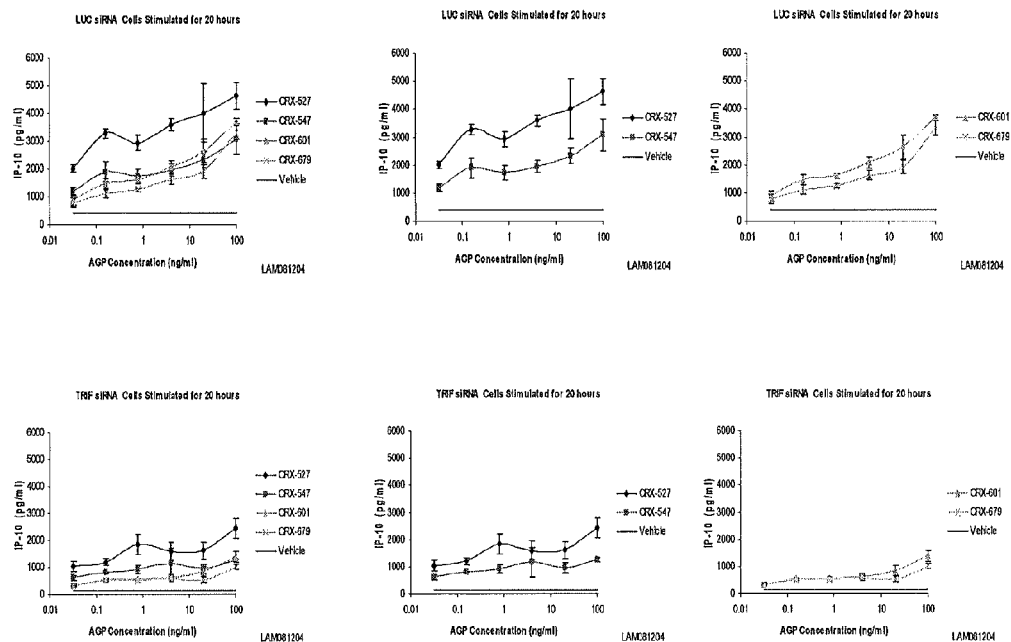
Figure 32. IP-10 Production after 20 hours of stimulation with L and D isomers (siRNA cell lines compared with the irrelevant control in each experiment).

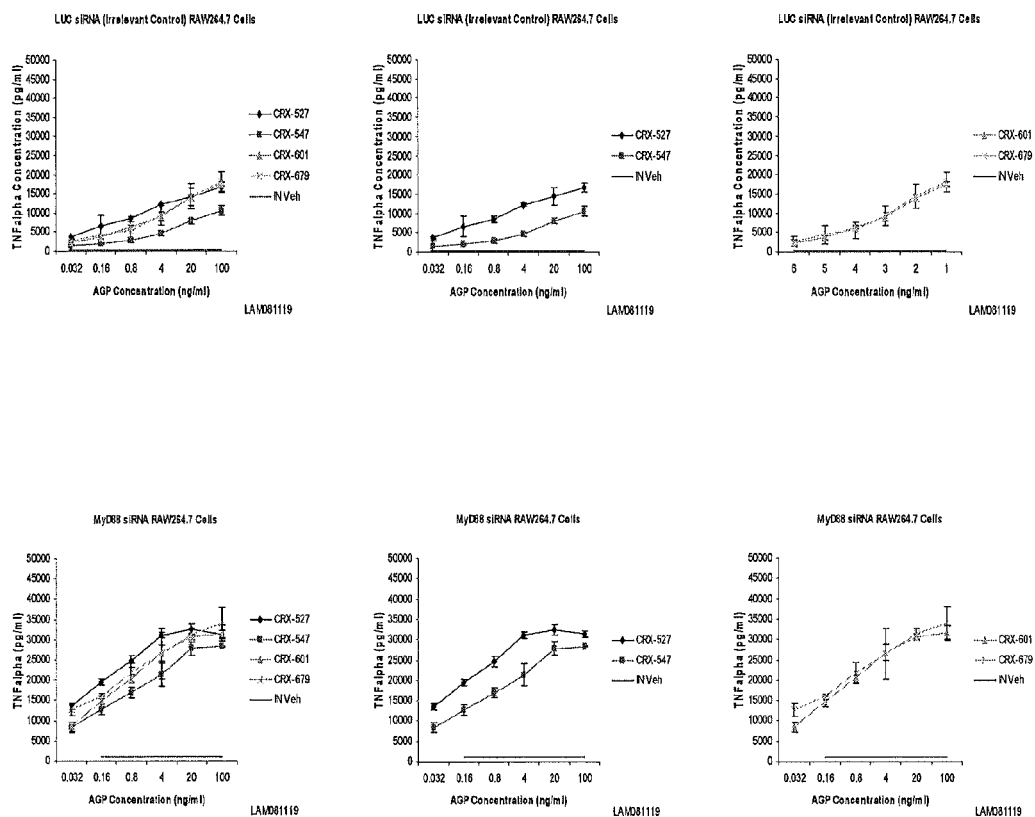
Figure 33. TNFα production after 20 hours of stimulation with L and D isomers

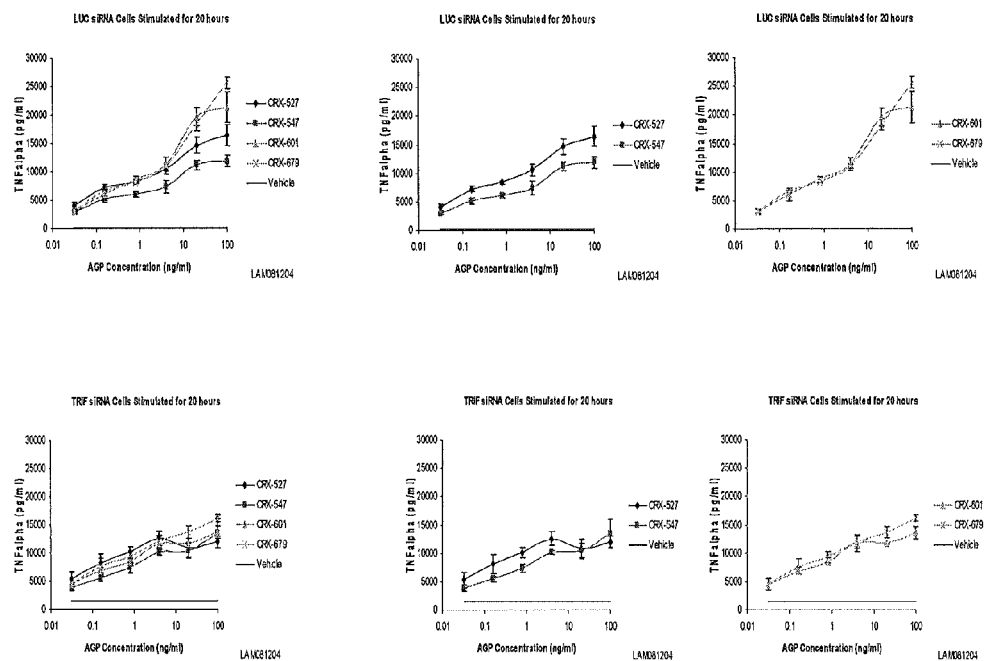
Figure 34. TNFα production after 20 hours of stimulation with L and D isomers

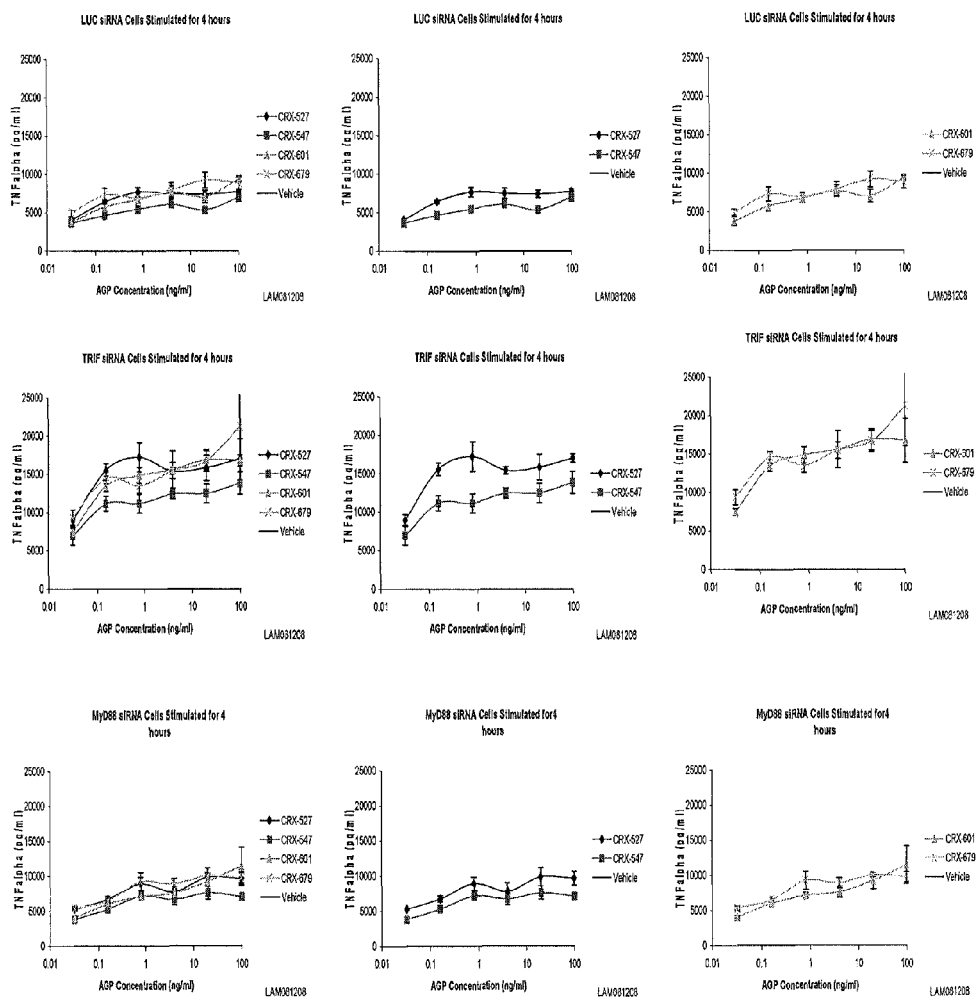
Figure 35. RAW264.7 siRNA cell lines stimulated for 4 hours with CRX-527, CRX-547, compounds 1a and 1b for TNFα production

METHOD FOR INDUCING A TRIF-BIAS

CROSS-REFERENCE TO RELATED APPLICATIONS

This application is filed pursuant to 35 USC 371 as a United States National Phase Application of International Patent Application Serial No. PCT/US2009/069465 filed on Dec. 23, 2009, which claims the benefit of U.S. Provisional 61/140,226 filed Dec. 23, 2008, which is incorporated herein by reference in its entirety.

STATEMENT REGARDING FEDERALLY SPONSORED RESEARCH

Aspects of this invention were made with United States government support pursuant to contract #HHSN266200400008C/N01-AI-40008 from National Institute of Allergy and Infectious Diseases; the United States government may have certain rights in the invention.

COPYRIGHT NOTIFICATION PURSUANT TO 37 C.F.R. §1.71(E)

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND

Toll-like receptors (TLR) are pattern recognition receptors that recognize conserved microbial motifs, including peptidoglycan (TLR2), CpG DNA (TLR9), viral RNA (TLR3/7/8), bacterial flagellin (TLR5) and LPS (TLR4). In particular TLR4s are characterized by a ligand-binding extracellular leucine-rich repeat domain and a cytoplasmic Toll-/IL-1R homology domain (Nahori et al., 2005) that recruits intracellular signaling adaptors. Several ligands for TLR4 have been described including lipopolysaccharid (LPS), lipoteichoic acid (LTA), fibronectin, the fusion protein of RSV, taxol and the vaccine adjuvant monophosphoryl lipid A (MPL). Two major signaling pathways associate with TLR4 activation have been described; the MyD88-dependent and TRIF-dependent pathways.

Recently it has been reported that the TLR4 ligand MPL, a derivative of a purified, detoxified glycolipid from the cell wall of *Salmonella Minnesota*, exhibited, a bias for TRIF-dependent signaling and less MyD88-dependent signaling relative to other TLR4 antagonists, and it was postulated that MPL may induce active repression of MyD88-dependent inflammatory pathways by inducing additional downstream signaling pathways such as the PI3-Kinase pathway. (Mata-Haro et. al. 2007).

A method is provided for inducing a relatively TRIF biased response comprising administering a selected isomer of an aminoalkyl glucosaminide 4-phosphate (AGP). The selective induction of TRIF-dependent signaling by synthetic lipid A mimetic as disclosed herein may allow for the development of vaccine adjuvants or immunomodulators that selectively alter immune responses while mitigating the potentially toxic side effects associated with the induction of inflammatory cytokines/chemokines.

SUMMARY OF THE INVENTION

The present invention is directed to the use of a synthetic lipid A mimetic, specifically the AGP compound CRX 547, to induce TRIF-biased signaling through the TLR4 receptor complex. CRX 547 is the diastereomer of AGP CRX 527. The term "TRIF-bias" refers to the reduction in MyD88 dependent signaling of a compound (e.g. CRX 547) relative to the MyD88 dependent signaling of another compound (e.g. CRX527). In a preferred embodiment the TRIF bias provides reduced MyD88 signaling and maintains or increases the TRIF dependent signaling. In other preferred embodiments the present invention may exhibit TRIF bias by inducing significant levels of the Th1 cell-mediated immunity-directing cytokine, IL-12, from dendritic cells, in vitro as well as inducing far less of the inflammatory mediator IL-23, a cytokine that favors the maintenance of Th17-T cells that produce the inflammatory mediators, IL-17 and TNFα (Wilson et. al. 2007). Th17-T cells have been linked to the development of inflammatory autoimmune disorders, including arthritis, inflammatory bowel disease, and multiple sclerosis (McGeachy et. al. 2007).

Several embodiments of the present invention are briefly described herein:

a method of significantly reducing the potential for MyD88-dependent signaling induced by a composition containing the L-seryl AGP CRX 527, while inducing significant TRIF-dependent signaling through the TLR4 receptor complex comprising substituting the D-seryl derivative of the L-seryl AGP in the composition;

a method of inducing TRIF-dependent cytokines and reducing levels of MyD88-dependent cytokines induced in human cells by a lipid A mimetic adjuvant composition comprising; administering CRX547 to human cells;

a method of inducing lower levels of IL-12p70 and IL-23 in human cells compared to levels induced by the L-seryl AGP CRX 527, comprising administering to human cells the synthetic D-seryl derivative of CRX527:

a method of activating significantly lower levels of NF-κB activity, but equal or higher levels of IRF3 induced by CRX527, comprising administering the D-seryl diastereomer of 527;

a method of inhibiting MyD88-dependent cytokine induction by a first lipid A mimetic comprising administering a second synthetic lipid A, CRX547; and a method of improving an adjuvant compositions induction of beneficial TRIF-dependent signaling in human cells, wherein the adjuvant composition contains an AGP which is not CRX547, comprising incorporating CRX547 into the adjuvant composition.

a lipid A mimetic composition comprising CRX547 for use in raising an immune response in a human wherein TRIF-dependent cytokines are increased and MyD88-dependent cytokines and decreased compared to a lipid A mimetic composition in the absence of CRX547;

a lipid A mimetic composition comprising CRX547 for use in raising an immune response in a human wherein NF-κB activity is decreased, but equal or higher levels of IRF3 are observed compared to a lipid A mimetic composition in the absence of CRX547;

a lipid A mimetic composition comprising CRX547 for use in raising an immune response in a human wherein IL-12p70 and IL-23 levels are decreased compared to a lipid A mimetic composition in the absence of CRX547;

An lipid A mimetic adjuvant for use with an antigen in raising an immune response in a human wherein IL-12p70 and IL-23 levels are decreased compared to a lipid A mimetic adjuvant in the absence of CRX547;

Lipid A mimetic compositions comprising CRX547 and CRX547 for use in any of the methods as described herein.

BRIEF DESCRIPTION OF THE DRAWINGS

FIG. 1. CRX-527 and CRX-547 and Aminoalkyl glucosaminide 4-phosphates with ester-linked fatty acyl chains, CRX-527 and CRX-547

FIG. 2. Comparison of the lipid A mimetics, CRX-527 and CRX-547 with *S. minn.* Re595 LPS for induction of (A) MyD88-dependent and (B) TRIF-dependent cytokines and chemokines in human PBMCs.

FIG. 3. Induction of (A) IL-12p70 and (B) IL-23, by treatment of human monocyte-derived dendritic cells with *S. minn.* Re595LPS, CRX-527 and CRX-547.

FIG. 4. Inhibition of (A) MyD88- and (B) TRIF-dependent cytokine/chemokine induction in a human macrophages cell line by transfection of plasmids expressing dominant negative constructs of MyD88 (MyD88-DN) and TRIF (TRIF-DN)

FIG. 5. (A) MyD88-dependent (MIP-1α) and (B) TRIF-dependent (RANTES) cytokines/chemokines induced by CRX-527, CRX-547, and LPS in the presence of the endocytosis inhibitor, Dynasore.

FIG. 6. ImageStream gating strategy.

FIG. 7. Human monocytic cells (MM6) were treated for 5, 15, 30, or 120 minutes with either CRX-527 or CRX-547 and nuclear translocation of NFκB was quantified as co-localization of the transcription factor with the nuclear dye (DRAK-5).

FIG. 8. Comparison of NF-κB-inducible promoter activity when huTLR4/huMd-2/huCD14-transfected HEK293 cells are treated with *S. minn.* Re595LPS, CRX-527, and CRX-547.

FIG. 9. Inhibition of CRX-527 and LPS (A) MyD88-dependent and (B) TRIF-dependent cytokine/chemokine induction in the presence of increasing concentrations of CRX-547.

FIG. 10. (A) Inhibition of CRX-527-induced TNFα by the addition of increasing concentrations of CRX-547. (B) Schild regression analysis yields an estimate of CRX-547 affinity (0.33 nM) similar to the $EC_{50}$'s of both CRX-527 and CRX-547.

FIG. 11. Inhibition of CRX527 and LPS MyD88-dependent (TNFα) cytokines induction in the presence of increasing concentrations of CRX547.

FIG. 12. Inhibition of CRX527-induced NFκB nuclear translocation in the presence of increasing concentrations of CRX547.

FIG. 13. Effects of stability-enhancing modification of CRX-527/CRX-547 on signaling activity and chemokine induction. Comparison of (A) NFκB signaling in huTLR4/huMD-2/huCD14-transfected HEK293 cells and, (B) MyD88-dependent MIP-1β induction in human monocytic cells (MM6), by the L and D isomer pairs CRX-527/CRX-547 and 1a/1b.

FIG. 14. Western Blot analysis of human primary, PBMC-derived monocytes treated with CRX-527 showing similar kinetics and levels of activation of phosph-IRF3 downstream of TRIF and greater degradation of IRAK1 downstream of MyD88 than cells stimulated with CRX-547

FIG. 15. Western Blot analysis of MM6 cells treated with CRX-527 showing greater degradation of IRAK4 downstream of MyD88 than cells stimulated with CRX-547

FIG. 16. Comparison of (A) NFκB signaling in huTLR4/huMD-2/huCD14-transfected HEK293 cells and, (B) MyD88-dependent MIP-1β induction in human monocytic cells (MM6), by the L and D isomer pair, compounds 2a and 2b.

FIG. 17. Induction of NFκB-dependent promoter activity by CRX-527, CRX-547, and LPS in HEK293 cells transfected with either human (top) and mouse (bottom) TLR4/MD-2/CD14

FIG. 18. Induction of NFκB-dependent promoter activity in HEK293 cells transfected with either cognate human/mouse TLR4/MD-2 or chimeric combinations (huTLR4/muMD2 or muTLR4/huMD-2).

FIG. 19. Weight change in rabbits treated with the indicated agonists

FIG. 20. Post-vaccination temperature in rabbits treated with the indicated agonist FIG. 21. Injection site reactivity by Draize in rabbits treated with indicated agonists FIG. 22. Injection site histopathology in rabbits treated with indicated agonists Weight change in rabbits treated with the indicated agonists FIG. 23. Induction of (A) MyD88-dependent, and (B) TRIF-dependent cytokine/chemokine gene expression in human PBMC-derived monocytes after treatment with 0.01 uM CRX-527 or CRX-547

FIG. 24. PBMCs from BALB/c Mice tested with CRX-547 (two lots) and CRX-527 (experiment performed once).

FIG. 25. Induction of TRIF-dependent (IP-10) by CRX-527, CRX-547, Compound 1a and 1b FIG. 26. Induction of MyD88-dependent (TNFα) cytokine/chemokine by CRX-527, CRX-547, compound 1a and 1b.

FIG. 27. TNFα levels after four hours of stimulation with AGPs and their D isomers.

FIG. 28. IP-10 levels after four hours of stimulation with AGPs and their D isomers.

FIG. 29. Western Blot analysis of Signaling Proteins after CRX-547 and CRX-527 stimulation in RAW264.7 Cells FIG. 30. Stably-transfected RAW264.7 Cells FIG. 31. IP-10 Production after 20 hours of stimulation with L and D isomers (siRNA cell lines compared with the irrelevant control in each experiment).

FIG. 32. IP-10 Production after 20 hours of stimulation with L and D isomers (siRNA cell lines compared with the irrelevant control in each experiment).

FIG. 33. TNFα production after 20 hours of stimulation with L and D isomers

FIG. 34. TNFα production after 20 hours of stimulation with L and D isomers

FIG. 35. RAW264.7 siRNA cell lines stimulated for 4 hours with CRX-527, CRX-547, Compounds 1a and 1b for TNFα production

DETAILED DESCRIPTION

Introduction lipid A is the active, hydrophobic structural motif within the LPS molecule that binds to the membrane-bound TLR4/MD-2 receptor complex. lipid A structures can show considerable variability between bacterial species. Individual gram-negative species can modulate the structure of the lipid A on their surface, resulting in varying degrees of inflammation (Bishop et al. 5071-80; Guo et al. 189-98). Changes in the number and length of acyl chains and the pattern of phosphorylation have been shown to dramatically alter the activity of lipid A molecules from highly potent agonists to antagonists {Hawkins, 2002 30067/id, Stover at al, Seydel et. al. 2000}.

The toxicity of most LPS species is determined by the interaction of the lipid A portion with the TLR4 receptor complex (Baker et al. 1992). Differences in acyl chain number, length, and arrangement, as well as the number and position of charged groups have all been shown to significantly affect both the level and character of the immunological response to lipid A (Teghanemt et al. 2005, Stover et. al. 2004, Schromm et al. 1998). The design and synthesis of a library of monosaccharide, lipid A mimetics, the aminoalkyl glucosaminide phosphates (AGPs), with TLR4 agonist and antagonist activity have also been described (Stover et al. 4440-49; Persing et al. S32-S37; Johnson et al. 2273-78).

As mentioned above, two major signaling pathways have been described following TLR4 activation by a TLR4 agonist; the MyD88-dependent and TRIF-dependent pathways. MyD88-dependent signaling depends upon sequential or simultaneous binding of the two Toll/interleukin-1 receptor (TIR) domain-containing adaptor proteins, Mal/TIRAP and MyD88, to the TIR domain of TLR4 (Fitzgeral et. al. 2001). TRIF-dependent signaling requires sequential or simultaneous binding of the TIR domain-containing adaptor proteins, TRAM/TICAM-2 and TRIF/TICAM-1, to the TLR4-TIR domain (Rowe et al. 6299-304; Yamamoto et al. 1144-50). Both pathways are involved in linking innate and adaptive immunity (Kawai et. al. 2001, Kaisho et al. 2001).

Downstream of the lipid A-receptor interaction, the specific TLR4-dependent signaling pathways, (the MyD88-dependent and TRIF-dependent pathways) determine the cellular response to receptor binding. MyD88-dependent signaling favors an inflammatory response, characterized by the synthesis and secretion of inflammatory mediators such as TNFα and IL-1β (Huang et. al. 2004). Signaling through the MyD88-dependent pathway induces early NF-κB activation and release of pro-inflammatory cytokines such as tumor necrosis factor alpha (TNF-α), interleukin (IL)-1β and the chemokine, MIP-1α.

TRIF-dependent signaling favors production of immune mediators such as Type 1 IFNs, some IL-12 family members and chemokines that induce dendritic cell maturation and influence T-cell maturation. Signaling through the TRIF-dependent pathway induces lower and later, but more sustained activation of NF-κB (Hoebe et al. 743-48) than does signaling through the MyD88 pathway, and induces activation and nuclear translocation of interferon regulatory factors (IRF)-3 and IRF-7 (Kawai et al. 5887-94). IRF-3 and IRF-7 activation drives transcription of IFNβ and its subsequent extracellular release. Autocrine or paracrine binding of IFNβ to the IFN-α/β receptor, in turn, activates the JAK/STAT pathway, leading to increased expression of IFNα and IFNβ, as well as IFN-inducible chemokines such as interferon-inducible protein-10 (IP-10), regulated on activation normal T expressed (RANTES), and macrophage chemotactic protein-1 (MCP-1) (Yamamoto et. al. 2003, Kawai et. al. 2001, Serbina et. al. 2003).

Most AGPs signal through both the MyD88- and TRIF-dependent pathways. It has recently been determined that a unique and interesting D-seryl AGP, CRX-547, signals predominantly through the TRIF-dependent pathway. This is in contrast to its stereoisomer, the L-seryl AGP CRX-527, which stimulates both the MyD88- and TRIF-dependent paths. Since the MyD88 pathway is associated with the induction of inflammatory cytokines while the TRIF dependent pathway leads to the production of type I interferons, the utilization of the TRIF pathway and avoidance of the MyD88 pathway may affect both efficacy and safety of TLR4 agonists when, for example, they are used as adjuvants. A relative increase in TRIF signaling may lead to enhanced cell mediated immunity while a relative decrease in MyD88-dependent signaling could lead to improved safety (lower induction of inflammation) and therefore a better therapeutic index for the D-seryl isomer relative to the L-seryl isomer.

Terms

Unless otherwise explained, all technical and scientific terms used herein have the same meaning as commonly understood by one of ordinary skill in the art to which this disclosure belongs. Definitions of common terms in molecular biology can be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

The singular terms "a," "an," and "the" include plural referents unless context clearly indicates otherwise. Similarly, the word "or" is intended to include "and" unless the context clearly indicates otherwise. The term "plurality" refers to two or more. It is further to be understood that all base sizes or amino acid sizes, and all molecular weight or molecular mass values, given for nucleic acids or polypeptides are approximate, and are provided for description. Additionally, numerical limitations given with respect to concentrations or levels of a substance, such as an antigen, are intended to be approximate. Thus, where a concentration is indicated to be at least (for example) 200 pg, it is intended that the concentration be understood to be at least approximately (or "about" or "~") 200 pg.

Although methods and materials similar or equivalent to those described herein can be used in the practice or testing of this disclosure, suitable methods and materials are described below. The term "comprises" means "includes." Thus, unless the context requires otherwise, the word "comprises," and variations such as "comprise" and "comprising" will be understood to imply the inclusion of a stated compound or composition (e.g., nucleic acid, polypeptide, antigen) or step, or group of compounds or steps, but not to the exclusion of any other compounds, composition, steps, or groups thereof. The abbreviation, "e.g." is derived from the Latin exempli gratia, and is used herein to indicate a non-limiting example. Thus, the abbreviation "e.g." is synonymous with the term "for example."

"lipid A mimetic" is a TLR4 ligand that induces TRIF and or MyD88 signaling through the TLR4 receptor (e.g. MPL and AGP).

"TRIF-bias" means lower levels of MyD88 dependent signaling by one compound as compared to another.

In order to facilitate review of the various embodiments of this disclosure, the following explanations of terms are provided. Additional terms and explanations can be provided in the context of this disclosure.

Aminoalkyl Glucosaminide 4-Phosphates

Briefly, the seryl AGPs CRX 527 and CRX 547 and are a class of lipid A mimetics in which the reducing sugar of lipid A has been replaced with an aminoalkyl L- or D-serine-based unit as well as three (R)-3-n-alkanoyloxytetradecanoyl residues comprised of 10 carbon normal fatty acyl chains. The AGPs are prepared as described previously by a highly convergent method, which allows chemical differentiation of the hydroxyl and amino groups and sequential introduction of the (R)-3-nalkanoyloxytetradecanoyl residues. (See Bazin et al. Bioorg. Med. Chem. Lett. 2008 18, 5350; Johnson et al Bioorg. Med. Chem. Lett 9 1999 2273; Patent Publication WO 04/005308). The seryl AGPs are purified by flash chromatography on silica gel (to >95% purity) and analyzed as their triethylammonium salts by standard analytical methods.

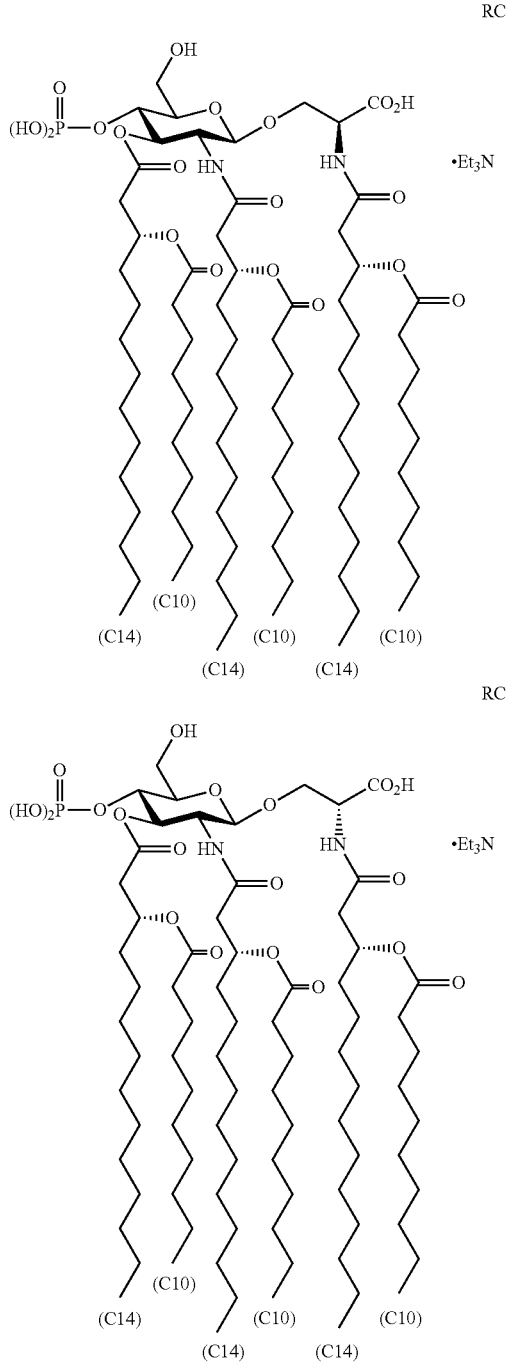

CRX527 and CRX547 also shown in FIG. 1 and have been synthesized and described previously (See U.S. Pat. No. 6,113,918; Examples 15 and 16, and WO 2006/012425 WO 2006/016997). The structural difference in CRX547 affects the position of the aglycon carboxyl group relative to that of CRX527. The difference may affect the interaction of the charged carboxyl group with the TLR4 receptor complex. LPS mimetics have previously been shown to interact with the TLR4 receptor complex through MD2 (Ohto et. al. 2007), therefore it is possible that the diasteroomeric difference between CRX547 and CRX 527 may disrupt interactions of the carboxyl group, a lipid A phosphate bioisostere, with MD-2 or TLR4. This could, in turn disrupt receptor dimerization or alternatively, an intracellular conformational change favoring binding of MyD88 and downstream signaling. Presumably, this disruption or change does not eliminate TRIF-dependent signaling.

Recently published crystal structures of the human TR4/MD-2/lipidIVa (Ohto et al. (2007) Science. 316:1632) and human TLR4/MD-2/Eritoran receptor suggests that the phosphate group at position one of the reducing sugar of the these lipid A mimetics interacts with charged groups near the opening of the MD2 hydrophobic binding pocket for lipid A. Structural modeling of TLR4/MD-2 dimerization with a second TLR4/MD-2 complex (Kim et al. 906-17; Walsh et al. 1245-54) suggests that this face of the MD-2/lipid A complex may interact with TLR4 of the dimer partner. The bio-isosteric carboxyl group of CRX527 may maintain these interactions, while the change to the diasteriomeric CRX547 might disrupt them, potentially inducing signaling differences.

It is noted that MPL, when tested, displayed the same patterns of MyD88- and TRIF-dependent signaling as CRX547, and MPL lacks a phosphate in the same position affected by the structural change in CRX547. Therefore, MPL and CRX547 may share a common mechanism for inducing TRIF-dependent signaling in the absence of substantial MyD88-dependent signaling.

Materials and Methods

The materials and methods described herein are useful in carrying out the Examples provided below.

Cell Line and Reagents

The HEK293 cell line expressing human TLR4, MD-2, and CD14, the NF-κB/LacZ reporter plasmids, the dominant negative MyD88-expressing (pDeNy-hMyD88) and dominant negative TRIF-expressing (pDeNy-hTRIF) plasmids, LyoVec transfection reagent and ultrapure Re595LPS from S. minnesota are obtainable from InvivoGen. The human monocyte/macrophage cell line, THP-1, are obtainable from ATCC. Fugene 6 transfection reagent is obtainable from Roche. HEK293-hTLR4/hMD2/hCD14 cells from InvivoGen (San Diego, Calif.) are cultured in RPMI 1640 (ATCC) with 10% FBS (Hyclone) with 10 μg/mL Blasticidin and 50 μg/mL HygroGold (InvivoGen). THP-1 cells are cultured in RPMI 1640 (ATCC) with 10% FBS (Hyclone) and 100 U/mL penicillin/100 ug/mL streptomycin (Sigma).

Primary Human Cell Culture

Peripheral blood mononuclear cells (PBMCs) are isolated from the blood of healthy donors via a Ficoll Hypaque 1.077 gradient and treated with agonists or are used to isolate adherent monocytes in monocyte media (RPMI 1640 (ATCC), 10% human AB serum (Lonza/BioWhittaker), 100 U/mL penicillin/100 ug/mL streptomycin (Sigma), 50 uM 2-mercaptoethanol (Sigma) as described (Stover et al. 4440-49; Kawai et al. 5887-94; Gervassi et al. 7231-39). Monocyte-derived macrophages are produced by incubating adherent monocytes for 5 days in monocyte media with 50 ng/mL rhM-CSF (R&D Systems) with media changes at day 3 and day 5 before agonist treatment. Monocyte-derived dendritic cells (DC) are produced by incubating adherent monocytes for 7 days in monocyte media with 10 ng/mL rhGM-CSF and 10 ng/mL rhIL-4 (R&D Systems) with media changes on day 3 and day 6.

NFkB Nuclear Translocation

MonoMac6 Cells in exponential growth are stimulated with increasing concentrations of AGP diluted in 2% glycerol vehicle for the indicated time points. Immediately fixed cells (in 2% paraformalin overnight) are stained with the primary antibodies, anti-NFκB(p65) (SantaCruz Biotechnology, SantaCruz, Calif.) and anti-IRF3 (BD Biosciences, San Jose, Calif.), in permeabilization buffer (PBS, 2% FBS, 0.1% TritonX) followed by secondary antibodies, anti-Rabbit FITC (Jackson Labs, Bar Harbor, Me.), anti-mouse PE (BD Biosciences, San Jose, Calif.). Similarity scores of signaling protein localization with the nuclear stain DRAQ5 (Alexis Biochemicals (San Diego, Calif.) are used for ImageStream analysis of Nuclear Translocation as previously described {George, 2006 32669/id}. A minimum of 3000 cells are collected and analyzed for each condition tested.

Dominant Negative MyD88 and TRIF

THP-1 cells are seeded in 12-well plates ($5 \times 10^5$ cells/well) and incubated in 0.5 mL RPMI 1640 (ATCC) with 100 U/mL penicillin/100 ug/mL streptomycin (Sigma) with 20 ng/mL phorbol mystyric acid (PMA) (InvivoGen) for differentiation into macrophages. After differentiation of the THP-1, the media is changed to THP-1 media with 5 ng/mL PMA and the cells are transiently transfected with 0.5 μg/well of the pDeNy-hMyD88/LacZ, pDeNy-TRIF/LacZ, or pUNO-mcs (control)/LacZ plasmids and Fugene 6 transfection reagent for 48 h. Media is exchanged for fresh media and the cells are then stimulated with the indicated concentrations of TLR4 agonists for 14 hours. Harvested supernatants are assayed for cytokine levels by multiplex sandwich ELISA (R&D Systems) with the luminex platform. Control wells are assayed for transfection efficiency using the Invivogen LacZ Quantitation Kit.

siRNA Knockdown of MyD88 and TRIF (MAL/TRAM)

Exponentially growing RAW264.7 cells are stably transfected with FuGene 6 by conventional methods in Optimem (Roche, Indianapolis Ind.) with psiRNA-mTICAM1, psiRNA-mMyD88, or psiRNA-LUC (irrelevant control) plasmids containing shRNA sequences for protein knockdown, a Zeocin resistance gene and a GFP coding sequence (InVivoGen, San Diego, Calif.). Transfection efficiency after selection is determined by percent GFP positive cells using the ImageStream.

HEK293 Transfections

HEK293-hTLR4/hMD2/hCD14 cells are seeded in 12-well plates ($4 \times 10^5$ cells/well) and are cultured until 40-60% confluent (2-3 days). The cells are transfected for 24 hours with 100 ng of NF-κB reporter construct expressing secreted human embryonic alkaline phosphatase under the control of an engineered ELAM promoter with five NF-κB sites (pNiFty2-SEA-InvivoGen; San Diego, Calif.) and a transfection control plasmid constitutively expressing a thymidine kinase promoter driven luciferase (Promega). Plasmids are prepared with the Endofree Maxiprep Plasmid kit from Qiagen. After transfection, cells are stimulated for 14 h with TLR4 agonists, and the cleared supernatant is assayed for SEAP activity (SEAP Reporter Assay Kit-InvivoGen) to quantify NF-κB activation and luciferase activity (Promega) to normalize for transfection efficiency following supplied protocols.

Dependence of CRX-547 Signaling on Endocytosis: Dynasore Inhibition.

Differentiated THP-1 macrophages (5E5/well in 48-well plates with 20 ng/mL PMA) are pre-treated with 10 uM Dynasore, a small molecule inhibitor of endocytosis for 60 minutes in serum-free THP-1 media. The media is changed to 0.45 mL THP-1 media before stimulation for 8 hours with the specified concentrations of agonists. Supernatants are collected and stored at −80 C before cytokine/chemokine analysis by multiplex sandwich ELISA (R&D Systems) using the Luminex platform.

Western Blot Analysis

For Western blot and phospho-Western blot protein analysis, cells are lysed with Cell Lysis Buffer (Cell Signaling Technology, Danvers, Mass.) with Protease Inhibitor Cocktail (Sigma, St. Louis Mo.). Western Blot on PVDF membranes (Millipore) is performed using standard methods. Bands are detected with ECL Advance Western Blot kit (GE Healthcare, Piscataway, N.J.). Secondary Anti-Rabbit HRP antibody is obtainable from KPL, (Gaithersburg, Md.). Anti-βactin, anti-IRF-3, anti-phospho-IRF-3 (Ser396) and anti-IRAK1 antibodies are obtained from Cell Signaling Technology (Danvers, Mass.).

Induction of Serum Cytokines/Chemokines in Mice

Female BALB/c or C57Bl/6 mice are obtained from Charles River Laboratories, USA, and are 7 to 9 weeks of age when the experiments are initiated. Mice are injected intraperitoneally with 200 uL of agonist in vehicle (0.2% glycerol) or vehicle alone. Serum samples are drawn at 2 or 6 hours post-injection and are tested for induction of cytokines/chemokines by multiplex sandwich ELISA (Invitrogen) on the Luminex platform. All animals are used in accordance with guidelines established by the Public Health Service and the Institutional Animal Care and Use Committee at GlaxoSmithKline Biologicals, Hamilton, Mont.

Rabbit Toxicology

Groups of three rabbits (NZW—Western Oregon Rabbit Company, Philomath, Oreg.) are vaccinated with 1 mL diluted AGP, or MPL control, IM on days 0, 7 and 14. Two doses of AGP are evaluated. All animals are monitored for body weight, temperature, clinical condition and draize score. Animals are sacrificed one week post final administration. Blood is collected pretreatment, two days after the $2^{nd}$ vaccination and upon sacrifice for hematology and clinical chemistry. Histopathology of injection sites and major organs are conducted according to standard practices. All animals are used in accordance with guidelines established by the Public Health Service and the Institutional Animal Care and Use Committee at GlaxoSmithKline Biologicals, Hamilton, Mont.

EXAMPLES

Example 1

Similar Levels of TRIF-Dependent, but Much Lower Levels of MyD88-Dependent Cytokines by Administering the D-Isomer of a Synthetic Lipid a Mimetics (CRX547) Relative to the L-Isomer (CRX527)

When the effects of S. minnesota Re595LPS, CRX-547 and CRX-527 on cytokine induction from fresh human peripheral blood mononuclear cells (PBMCs) are compared, CRX-527 and LPS induce similar levels of the cytokine TNFα and chemokine MIP-1α (FIG. 22A). Alternatively, CRX-547 induces significantly lower levels of TNFα and MIP-1α, but comparable levels of the chemokines IP-10 and RANTES (FIG. 22B).

Expression of TNFα and MIP-1α are dependent upon signaling through the TLR4 adaptor, MyD88, while expression of IP-10 and RANTES are dependent upon signaling through the TLR4 adaptor, TRIF/TICAM-1 (Hoebe et al, Kawai et al). When the agonists are compared for induction of the same set of MyD88-dependent and TRIF-dependent cytokines in fresh human whole blood, cultured human monocytes, human monocyte-derived macrophages, and human monocyte-derived dendritic cells, a similar pattern of results is observed (data not shown).

Example 2

CRX-547 Induces Lower Levels of IL-12p70 and IL-23 in Monocyte-Derived Dendritic Cells Induction of inflammatory cytokines and maturation of dendritic cells (DC) contribute to the promotion of a robust immune response during the administration of an adjuvanted vaccine. Therefore, the capacity of CRX527 and CRX-547 to induce IL-12p70 in human DCs is compared. The induction of IL-12p70 promotes the development of the Th1 helper T cell lineage and favors development of a cell-mediated immune response (Goriely, Neurath, and Goldman 81-86; Gutcher and Becher 1119-27). As expression of IL-12p70 has been shown to be both MyD88 and TRIP signaling dependent (Goriely, Neurath, and Goldman 81-86), it can be verified whether the response of DCs to CRX547 treatment might be abrogated. Although significantly reduced when compared to CRX-527 and LPS, CRX-547 may induce an IL-12p70 response from human monocyte-derived DC (FIG. 3A).

Alternatively, the expression of the inflammatory mediator, IL-23, in DC is wholly MyD88-dependent (Re and Strominger 37692-99; Goriely, Neurath, and Goldman 81-86). When the induction of IL-23 by treatment of dendritic cells with CRX-527 and CRX-547 is compared, it is found that IL-23 expression is reduced virtually to base-line levels in CRX-547-treated cells. (FIG. 3B).

Example 3

MyD88 and TRIF Dependence of Cytokine Induction

When expression of a dominant negative mutant construct is used to inhibit signaling through MyD88, induction of MyD88-dependent cytokine, TNFα, by CRX-527 is significantly reduced, and induction of TRIF-dependent cytokine, RANTES, is only slightly reduced, while CRX-547 induction of MyD88-dependent cytokines is unaffected by knock down of MyD88 ([066]4A).

Alternatively, when expression of TRIF is knocked down using similar methods, the induction of TRIF-dependent cytokines by both CRX547 and CRX527 is reduced to a similar extent ([066]B).

MyD88/TRIF signaling specificities of the AGPs, CRX-527 and CRX-547 can also be differentiated by the dependence on endocytosis. Recently, two separate groups (Kagan et al. 361-68; Tanimura et al. 94-99) have reported that MyD88-dependent signaling downstream of TLR4 is initiated from the cell membrane, while TRIF-dependent signaling downstream of TLR4 is initiated from the endosome/lysosome after internalization of the TLR4 receptor complex. Kagan et al. used the endocytosis inhibitor, Dynasore, to show that TRIF-dependent, but not MyD88-dependent cytokine induction was inhibited. Therefore, Dynasore is used as shown below to compare the MyD88 and TRIF dependence of cytokine/chemokine induction by CRX-527 and CRX-547.

Inhibition of endocytosis with Dynasore inhibits TRIF-dependent RANTES induction by both CRX-527 and CRX-547 in human PBMC-derived macrophages (05), while induction of MyD88-dependent MIP-1α increases slightly relative to non-treated cells. These results suggest that TRIF-dependent cytokine induction by CRX-527 and CRX-547, downstream of TLR4, occurs by similar signaling mechanisms following endocytosis.

Example 4

CRX-547 Induces Significantly Lower Levels of NFκB Nuclear Translocation and Transcriptional Activity, but Equal or Higher Levels of IRF-3 Nuclear Translocation Compared to CRX527

Expression of many inflammatory cytokines, including TNFα and IL-1β, is dependent upon activation and nuclear translocation of the NFκB. Both MyD88-dependent and TRIF-dependent signaling downstream of the TLR4 receptor complex induce activation and nuclear translocation of the transcription factor, NFκB. However, NFκB activation through TRIF-dependent signaling is induced later and to a much lower extent than activation through MyD88-dependent signaling (Yamamoto et. al. 2002).

Interferon Response Factor-3 (IRF-3) is a transcription factor activated downstream of the TRIF-dependent TLR4 signaling pathway (Yamamoto et al. 640-43). IRF-3 phosphorylation leads to IRF-3 dimerization, nuclear translocation, and induction of transcription of Type I interferon (IFNβ) and interferon-inducible genes (Honda, Takaoka, and Taniguchi 349-60; Tailor, Tamura, and Ozato 134-40). The ImageStream is capable of measuring nuclear translocation of both NFκB and IRF-3 by quantification of co-localization between the labeled transcription factors and the nucleus of cells stained with a nucleus-specific dye (DRAK-4) (Beum et al. 90-99; George et al. 117-29; Arechiga et al. 7800-04).

In order to compare signaling initiated by CRX-527 and CRX-547, the induction of nuclear translocation of NFκB and IRF-3 by CRX-527 and CRX-547 treatment is compared in the human monocytic cell line, MonoMac6 (MM6) using ImageStream analysis. FIG. 6 shows the gating strategy for MM6 cells stimulated with CRX-527 and CRX-547.

CRX-527 induces earlier NFκB nuclear translocation (as early as 5 minutes post-stimulation) when compared to CRX-547. The NFκB nuclear translocation induced by CRX-547 activity never reaches above a certain threshold (in this case around 50%) whereas, by thirty minutes, CRX-527 stimulation results in nearly 100% nuclear translocation of NFκB (FIG. 7). Both AGPs appear to work in a dose-dependent manner. A high background level of IRF3 Nuclear translocation is present regardless of CRX-527 or CRX-547 stimulation suggesting both signal through TRIF (data not shown). Since early NFκB activity is indicative of a MyD88 signaling pattern, this data suggests that CRX-527 signals through MyD88 whereas CRX-547 is less potent at inducing MyD88 signaling.

To confirm that the nuclear translocation differences between CRX-527 and CRX547 translate into elevated transcriptional activation, CRX-527 and CRX-547 induced NFκB activation in HEK293 cells transfected with human TLR4, MD-2, CD14 and an NFκB reporter plasmid are compared. As in a nuclear translocation assay, it is found that CRX-527 and LPS induce significantly higher activation of the NF-κB promoter than CRX547 (FIG. 8).

CRX-527 signals through the TLR4/MD2 receptor complex leading to activation of transcription factors that lead to induction of cytokines and chemokines. When increasing concentrations of CRX-547 are added to primary human adherent monocytes prior to the addition of a fixed concentration of CRX-527 or LPS, induction of the MyD88-dependent cytokine, TNFα, is inhibited, while induction of the TRIF-dependent chemokine, MCP-1, is increased additively at higher concentrations of CRX-547. (FIG. 10). The concentration of CRX-547 required to inhibit TNFα induction is in the same range as the fixed concentrations of CRX-527 and LPS, suggesting that CRX-547 may compete with CRX-527 and LPS for binding to the TLR4 complex but primarily induces signaling through the TRIF pathway when bound.

As CRX-547 appear to be a partial agonist relative to CRX-527 and LPS for induction of MyD88-dependent cytokines/chemokines downstream of TLR4 in monocytic cells, the inclusion of CRX-547 when treating monocytic cells with CRX-527 may inhibit cytokine/chemokine induction and providing insight into the mechanism of action for TRIF-selective signaling by CRX-547. To that end, human primary monocytes are treated with a dose range of CRX-527 in the presence of increasing concentrations of CRX-547.

The resulting dose-response curves are fit with a 4 parameter logistic equation. FIG. 10A shows the effects of inclusion of 0 uM, 0.000016 uM, 0.004 uM, and 0.1 uM CRX-547 on the dose-response curves for CRX-527-induced TNFα.

As expected for a partial agonist, increasing concentrations of CRX-547 shift the TNFα induction curves out along the X axis (potency shift), while the basal level of the curves (bottom asymptote) increases to the response level of CRX-547 in the absence of CRX-527. Plotting the log $EC_{50}$ shift (DR-1) for each concentration of CRX-547 versus the log of the concentration of CRX-547 (Schild regression) allows us to compare the calculated affinity ($Kb_{app}$) with the $EC_{50}$ for CRX-547 calculated from the CRX-547 and CRX-527 dose-response curve. The values confirm that the affinity of CRX-547 approaches the $EC_{50}$'s of both CRX-547 and CRX-527 and suggests that CRX-547 effectively competes with CRX-527 for binding and MyD88-dependent signaling (leading to TNFα induction) at the TLR4 receptor complex. (FIG. 10B.)

Similarly, FIG. 11 shows when increasing concentrations of CRX-547 are added to primary human adherent monocytes simultaneously with the addition of a fixed concentration of CRX-527 or LPS induction of the MyD88-dependent cytokine, TNFα, is inhibited. The concentration of CRX547 required to inhibit TNFα induction is in the same range ($IC50_{CRX-527}$: 48±30 nM/$IC50_{LPS}$: 18±12) as the fixed concentrations of CRX527 and LPS (100 nM), suggesting that CRX547 competes with CRX527 and LPS for binding to the TLR4 complex.

To determine whether CRX-547 is able to antagonize NFκB nuclear translocation in cells treated with constant CRX-527, MM6 cells are stimulated for 20 minutes, 35 minutes and 2 hrs with increasing doses of CRX-547 (FIG. 12). When AGPs are added at the same time, CRX-547 antagonized NFκB nuclear translocation induced by CRX-527 at the highest doses. When CRX-547 is constant and spiked with CRX-527 into the assay, CRX-527 stimulation is able to overcome the maximal effect of NFκB nuclear translocation with CRX-547 alone. This data suggests that CRX-547 and CRX-527 compete for binding at the TLR4 receptor complex, leading to inhibition of MyD88-dependent signaling.

Example 6

Analogs of CRX-547 with Apparent TRIF-Biased Agonism of Human TLR4

In order to evaluate analogs in the AGP family, compounds are tested for similar patterns of cytokine/chemokine induction. L and D isomer pairs of the seryl AGPs, CRX-527 and CRX-547, with ester-linked secondary acyl chains are compared with the seryl analogs having ether-linked secondary acyl chains, compounds 1a and 1b, (compounds shown in FIG. 1), a potential stability-enhancing modification of the lead candidate AGPs. Interestingly, for 1b, modifying the molecule to have ether-, rather than ester-linked secondary acyl chains reinstates substantial efficacy in the D isomer relative to the L isomer for induction of MyD88-dependent signaling (FIG. 13). The mechanistic basis for this MyD88 efficacy rescue by the ether-linked D isomers is not known.

Example 7

Phospho-Western Blot Analysis of Human Primary Monocytes Stimulated with CRX-527 or CRX-547 and with MM6 Cells Stimulated with CRX-527 or CRX-547

Degradation of the Serine/Threonine Kinase, IRAK-1, occurs downstream of MyD88-dependent TLR4 signaling (Hatao et al, 260-64; Neumann et al. 1089-94), while TRIF-dependent TLR4 signaling results in IRF-3 activation (Yamamoto et al. 6668-72; Yamamoto et al. 640-43). Here, human primary monocytes are stimulated with either CRX-547 or CRX-527 for the indicated times, and cellular lysates are analyzed by Western Blot for the levels of the MyD88 pathway-activated kinase, IRAK-1, and the TRIF pathway-activated transcription factor, IRF-3 (phospho-IRF-3 and total IRF-3). The levels of β-actin is used as the loading control. CRX-527-stimulated monocytes show a rapid decrease in IRAK-1, whereas CRX-547 stimulated cells show delayed and reduced degradation of this protein (FIG. 14).

The role of MAPK signaling molecules in MyD88 versus TRIF signaling after TLR4 ligation is complicated because p38 is implicated in both pathways, however a role for p38 phosphorylation as an indicator of the TRIF pathway is indicated in the literature. The phosphorylation of p38 is reduced in macrophages from TRIF−/− mice after stimulation with LPS whereas TRIF+/+macrophages display sustained phosphorylation of p38, suggesting TRIF may play a role in maintaining the phosphorylation state of p38 after TLR4 ligation (Thomas et al. 31119-30). To determine whether the phosphorylation state of p38 is different after stimulation with CRX-527 versus CRX-547, western blot analysis is performed on lysates from MM6 cells. CRX-527 stimulation results in a slight increase in the phosphorylation state of p38 compared to CRX-547, although they show a similar kinetic of activation (FIG. 15).

MAPK pathways and downstream transcription factors are differentially regulated by TLR agonists. Degradation of IRAK4 and IκBα are indicative of MyD88 after TLR4 signaling (Hatao et al. 260-64; Neumann et al. 1089-94), while TRIF-mediated TLR4 signaling results in IRF3 activation (Yamamoto et al. 6668-72; Yamamoto et al. 640-43). MM6 cells are stimulated with either CRX-547 or CRX-527 (10 ng/ml) for the indicated time. Cellular lysates are collected and Western Blot analysis of the MyD88 pathway proteins, Phospho-IκBα, total IκBα, IRAK4, and TRIF pathway proteins, phospho-p38, total IRF3 and phospho IRF3 is performed using βactin as the loading control. CRX-527 stimulated MM6 cells have a rapid decrease in total IκBα and IRAK-4, whereas CRX-547 stimulated cells are delayed and less degradation of both of these MyD88-induced signaling proteins. In terms of the TRIF-mediated signaling proteins, phosphor-p38, total p38 IRF3 and phosphor-IRF3 little or difference between these two AGPs is observed.

Example 8

Evaluation of MyD88- and TRIF-Dependent Signaling in Mice

Contrary to results for human primary cells, CRX-547 induces similar levels of MyD88-dependent cytokines in mouse serum following IV administration in BALB/c mice. To ensure that this response is not specific to BALB/c mice, a similar test of serum cytokine induction in C57BL/6 mice is carried out. (FIG. 16). The kinetics (induction at 2 or 6 hours post injection) and magnitude of cytokine induction are similar for CRX-527 and CRX-547 for both MyD88-dependent (TNFα, IL-10) and TRIP-dependent (RANTES, IP-10, MIG) cytokines/chemokines, although the relative induction by CRX-547 is slightly less for select cytokines than that seen in BALB/c (not shown). Also of interest, induction of the MyD88-dependent cytokines tested is consistently higher at 2 hours than at 6 hours post-injection, while induction of TRIF-dependent cytokines is higher at 6 hours for each of the agonists, suggesting different kinetics for cytokine induction through the two pathways. This phenomenon could be explained by a requirement for early IFNβ induction and autocrine/paracrine activity observed previously for induction of many TRIF-dependent cytokines (Perry et al. 407-22), or by a delay in TRIF-dependent signaling due to the requirement for endocytosis (Kagan et al. 361-68).

Several examples of testing for MyD88- and TRIF-dependent cytokine/chemokine induction by the L and D isomer AGPs in vitro (see Examples 12-14 below). In each case, including cytokine induction in murine PBMCs, cytokine induction in the murine macrophage cells line, RAW264.7, and NFκB activity induction in muTLR4/muMD2-transfected HEK293 cells, the D isomers of the seryl AGPs, do not show the same TRIF signaling bias as is demonstrated in human systems disclosed herein.

Example 9

Receptor Basis for Species Specificity (Murine Vs Human) of CRX-547 Signaling Different signaling patterns for two AGP isomers are noted, with CRX-547, the D isomer of CRX-527, signaling in a TRIF-biased fashion while CRX-527 signals through both MyD88- and TRIF-dependent pathways. In initial studies, the TRIF-biased signaling of CRX-547 appeared to be species dependent as it was observed on human cells but not murine. To address this apparent difference, we utilize human and murine TLR4-, MD-2-, and CD14-transfected HEK293 cells and combinations thereof to test the receptor/co-receptor requirements and receptor species specificity for AGP signaling.

It is shown that HEK293 cells transfected with huTLR4, huMD-2, and huCD14 and stimulated with CRX-547 induce less NFκB reporter activity than CRX-527 and LPS, while the levels activity induced by CRX-547 in HEK293 cells transfected with muTLR4, muMD-2, and muCD14 were more similar to CRX-527 and LPS (FIG. 17). This analysis suggests a preference for a murine TLR4 receptor complex for induction of signaling by CR-X547. In order to determine whether TLR4 itself or another accessory receptor component is responsible for this species specificity, the analysis is expanded to include HEK293 cells expressing combinations of human and murine TLR4 receptor components.

As shown in FIG. 18, when HEK293 cells are transfected with a combination of human TLR4 and murine MD-2, there remains a large relative difference in the induction of promoter activity between CRX-527 and CRX-547, suggesting this disparity stems from a divergence in the interaction of CRX-527 and CRX-547 with human TLR4. When HEK293 cells are transfected with a combination of murine TLR4 and human MD-2, CRX-527 and CRX-547 induced similar levels of promoter activity, again suggesting the difference in activity may stem from a divergence in the interaction at the AGP/TLR4 interface. These results are different from the effect of modifications in acyl chain length and composition that caused differences in the interaction of the molecule with MD-2 seen by Moroi et. (Moroi, M. and Tanamoto, K. (2006), J. Biol. Chem. 281. p 5484-5491).

It should be noted that the levels of activity are much lower overall for chimeric complexes (huTLR4/muMD2, muTLR4/huTLR4) than when complexes with cognate receptor components are present (huTLR4/huMD2, muTLR4/muMD2), suggesting that these interspecies chimeras do not function optimally in this system. Further biochemical analysis will be required to elucidate specific residues that contribute to the purported species specificity of CRX-547.

Example 10

Rabbit Toxicology Study with Lead Candidate AGPs by IM Route

Toxicity of CRX-527, 524, 547 and compound 1 is evaluated in rabbits receiving AGP only by the intramuscular (IM) route. Groups of three rabbits are vaccinated with 1 mL diluted AGP, or MPL control, IM on days 0, 7 and 14. Two doses of AGP are evaluated: high (25 µg) and low (5 µg). All animals are monitored for body weight, temperature, clinical condition and draize score. Animals are sacrificed one week post final administration. Blood is collected pretreatment, two days after the $2^{nd}$ vaccination and upon sacrifice for hematology and clinical chemistry. Histopathology of injection sites and major organs are conducted.

All animals demonstrate weight gain throughout the course of the study with the exception of the MPL group between the $2^{nd}$ and $3^{rd}$ vaccinations (FIG. 19). Post-vaccination temperature variations ±~1° C. are noted, including the vehicle control group (FIG. 20). All temperatures are within in the normal range for rabbits. Minimal injection site reaction is noted by Draize scoring for all groups, including vehicle controls; and reaction decreases with increasing number of vaccinations (FIG. 21). Gross pathology of white discoloration of muscle along needle track and at site of injection is noted in all high adjuvant dose groups with the possible exception of CRX-524; pathology also seen in CRX-527 and compound 1, but not -524 or -547 treated groups at low dose.

Hematology analysis reveals a trend of granulocytosis in rabbits administered low and high doses CRX-527 and low dose CRX-524 and -compound 1 on day 9 (2 days post-2°) which resolves by day 21 (7 days post-3°). AGPs have been known to attract neutrophils. No trends in clinical chemistry values post-vaccination are noted.

Inflammation at the site of injection, consisting primarily of basophil and macrophage myositis, is the only non-incidental finding in all treatment groups with the exception of low dose CRX-547 where no muscle pathology is noted (FIG. 22-25). Myositis shows most consistent and greatest for high dose CRX-527. Myositis is also most consistent with injection sites from the most recent two injections indicating the transient nature of the inflammatory response (data not shown).

The overall impression is that CRX-547 is minimally toxic at high dose only and CRX-524, -527 & compound 1 are mildly toxic with low power (n=3 rabbits/group). Pathologic findings are transient.

Example 11

Cytokine Gene Expression in Response to CRX-527 and CRX-547 Treatment

To compare CRX-527 and CRX-547 for induction of cytokine/chemokine secretion in human cells and to further elucidate the signaling mechanisms responsible for the observed differences, gene expression induced by CRX-527 and CRX-547 is evaluated using microarray technology. Initial experiments include time course analysis of MyD88- and TRIF-dependent cytokine gene induction using qPCR. This analysis suggests that induction of MyD88- and TRIF-dependent cytokine/chemokine genes are detectable by 1-2 hour post-treatment for both agonists, rise to robust levels by 3 hours post-treatment, and decline to near base-line levels by 6 hours post-treatment (data not shown). Induction of both MyD88- and TRIF-dependent cytokine/chemokine genes tends to be highest at 3 hours post treatment, suggesting that a substantial kinetic difference between MyD88- and TRIF-dependent induction does not operate at the level of gene expression. One exception to the kinetic pattern is IFNβ induction, which is already at the highest level after 1 hour treatment with either CRX-547 or CRX-527 treatment and declines thereafter.

CRX-527 not only induces greater MyD88-dependent cytokine/chemokine gene expression, but greater TRIF-dependent cytokine/chemokine gene expression than CRX-547 in this analysis. This phenomenon does not correlate with the pattern observed for cytokine/chemokine protein secretion, where TRIF-dependent cytokine/chemokine secretion is similar for the two agonists This data may suggest that other factors affect the levels of TRIF-dependent cytokine/chemokine secretion induced by CRX-527 and CRX-547. One possibility is that CRX-547 treatment induces greater TRIF-dependent gene mRNA stability than CRX-527. Although the levels of these genes have decreased almost to base-line by 6 hours post-treatment (data not shown), we have not yet tested the levels of mRNA between 3 and 6 hours.
In Vitro Murine Systems Example 12

In Vitro Cytokine Induction

As was mentioned above, less TRIF biasing by CRX-547 is suggested in cytokine induction experiments with murine PBMCs, a murine cell line (RAW264.7) and HEK293 transfection studies (data not shown). Further comparison of cytokines induced by CRX-547 and CRX-527 in RAW264.7 cells using an expanded dose range and testing an additional L and D isomer pair, compounds 1a and 1b, with ether rather than ester-linked fatty-acyl chains are provided (FIG. 1). In addition, to gain a greater mechanistic understanding of the species specificity phenomenon, signaling induction by CRX-547 in cells transfected with chimeric human/murine TLR4 receptor complexes are compared. Such species-specific TLR4 antagonist/agonist activity has also been reported for lipidIVa, a lipid A precursor from *E. coli* with only 4 primary acyl chains (Muroi, Ohnishi, and Tanamoto 3546-50;

Muroi and Tanamoto 5484-91), and this activity was attributed to differences in the structure of the TLR4 accessory receptor MD-2 in mice.

To determine whether PBMCs from mouse blood have similar profiles of MyD88 cytokines after CRX-527 or CRX-547 treatment, commercially available blood from BALB/c mice is tested with CRX-527 or CRX-547. (FIG. 24), Levels appear to be similar between the two groups tested.

To better compare and confirm the similarity of potency between the L and D isomers in murine cells, RAW264.7 (macrophage) cells are stimulated over a wider dose range with CRX-527, CRX-547, compounds 1a and 1b and the supernatants assayed for MyD88 (TNFα) and TRIF-dependent (IP-10) production. CRX-527 is more potent at inducing both TNFα and IP-10 production than CRX-547 in this range (FIGS. 25 and 26). For this murine cell line, CRX-547 induction of both TRIF- and MyD88-dependent cytokines is less potent than for CRX-527. This data suggests that the species-specific activity of CRX-547 may not bet clear-cut, although the difference in activity of CRX-527 and CRX-547 for induction of MyD88-dependent cytokines in a human cell line is generally much larger than in murine cell lines, suggesting there are major differences in the interaction of CRX-547 with murine and human TLR4/MD2 receptor complexes.

Compounds 1a and 1b induce similar levels of TRIF- and MyD88-dependent cytokines in both murine and human cell lines suggesting that a change from ester- to ether-linked fatty acid chains combined with a change from the L to the D isomer of the aglycon seryl group rescues the activity of the D isomer in human cells. As both of these modifications change the relative position of charged groups on the AGP, the differences may be associated with differences in the interactions of the molecules with the TLR4/MD2 receptor complex.

Since MyD88-dependent signaling after TLR4 stimulation should be earlier than TRIF dependent signaling, and because both MyD88 and TRIF can induce downstream TNFα production due to activation of the NFκB pathway, an earlier timepoint is tested for cytokine production after stimulation with the L and D isomers. After four hours of stimulation, CRX-527 appears to be slightly more potent at inducing both TNFα and IP-10 production in RAW264.7 cells (FIGS. 27 and 28).

Example 13

Western Blot Analysis of Murine RAW264.7 Cells

To determine whether the phosphorylation (activation) status of key protein signaling molecules in the TRIF versus MyD88 in RAW264.7 cells, cells are pre-activated with $10^{-7}$M PMA) then stimulated with 10 ng/ml of the AGPs. Cellular lysates are prepared at 0, 15 m, 30 m, 45 m, 60 m, 120 m, 240 m, Similar to results in MM6 cells, IκBα degradation is faster after stimulation with CRX-527 compared to CRX-547 (FIG. 29). Surprisingly, CRX-547 stimulation results in a higher degree of IκBα phosphorylation and IRF3 phosphorylation. The increased reponsiveness of these cello could be due to the pre-activation with PMA, known to increase the maturation state of monocytic cells. CRX-547 induces expression of Phospho-IκBα and Phospho-IRF3. IRF3 is induced through TRIF mediated signaling. The amount of total IRF3 protein is also higher in the cells treated with CRX-547. (Note: The experiment was performed once and the loading control (βactin) suggests a possible uneven loading.)

Example 14

RNA Interference Analysis

RNA interference (RNAi) is utilized to disrupt expression of specific genes that are involved in TLR signaling pathways: TLR2, TLR4 and MyD88. RAW264.7 siRNA cell lines are prepared using commercially available plasmids (Invivogen). These plasmids contain a Zeocin selection marker, a sequence coding for GFP and the sequence coding for shRNA for knockdown. Once the cells are efficiently transfected, stable cell lines are generated through antibiotic selection. Purity of cultures is determined by GFP+ cells within the culture system. An irrelevant plasmid is also used to stably transfect cells as a control. FIG. 30 demonstrates knock down of MyD88 and TRIF in stable transfectants of the cognate siRNA. FIG. 30A shows that the percent of GFP positive cells prior to cytokine-readout experiments is more than 96% in all three cell lines. FIG. 30B shows evidence of successfully knock down for MyD88 and TRIF, as stimulation with LPS resulted in decreased protein levels compared to the irrelevant control.

To determine whether TRIF or MyD88 are required for the cytokine response after stimulation with L and D isomers, stably transfected siRNA cell lines are stimulated for 20 hours (in an assay similar to the MM6 potency assay) or 4 hours (to capture MyD88 induced cytokine responses) and cellular supernatants are assayed for TNFα (MyD88) and IP-10 (TRIF). Twenty hours post-stimulation, the irrelevant control, LUC cell line has a similar IP-10 induction pattern as the wt RAW264.7 cells shown previously. In the TRIF knockdown cells, IP-10 levels do not follow the same dose response observed with the irrelevant control, suggesting TRIF is required for efficient IP-10 responses after AGP stimulation. When TRIF is intact (in MyD88 knockdown cell lines) the IP-10 levels remain dose responsive and total cytokine is increased above the irrelevant control (LUC). Other assay systems (including human and mouse systems) support the hypothesis that both L and D isomers are efficient at inducing TRIF mediated cytokines.

In terms of TNFα, which is controlled by both MyD88 (early release of TNFα) and TRIF (delayed release of TNFα, due to delayed activation of NFκB), CRX-527 is more potent in the irrelevant control compared to CRX-547 (FIG. 31). When either MyD88 or TRIF are knocked down, this same increased potency of CRX-527 over CRX-547 is observed. Since TNFα is induced by both MyD88 and TRIF, the 20 hour time point does not allow for adequate discrimination between the signaling pathways after CRX-527 or CRX-547 stimulation. Together, this data suggests two possibilities; that in the time-frame tested, the induction of TNFα does not require MyD88, or that the siRNA knockdown of MyD88 is not sufficient to suppress TNFα. The hypothesis that TRIF signaling alone can induce TNFα, has some support; this induction is may be due to TRIF mediated signaling. Therefore, this induction of TNFα may be due to both MyD88 and TRIF mediated signaling. Compound 1a and CRX-679 have equivalent responses at 20 hours in both assay systems In order to better discriminate the MyD88 requirement for TNFα production, siRNA knockdown cell lines are examined for TNFα production after four hours of AGP stimulation (FIG. 35). Four hours post stimulation, CRX-527 and CRX-547 show a similar induction of TNFα in the irrelevant control cell line (LUC). Potency differences and the peak of TNFα production is enhanced in TRIF knockdown cells where TNFα production should be limited to MyD88 induction. MyD88 knockdown results in similar levels of TNFα production between the two AGPs. Taken together this data indicates a requirement for MyD88 early to induce TNFα production after stimulation with AGPs. Furthermore, CRX-527 is more potent at inducing TNFα than the equivalent dose of CRX-547. Compound 1a and 1b result in similar cytokine patterns. IP-10 levels after four hours of stimulation with RAW264.7 cells are very low, so siRNA cell lines were not assayed for IP-10 levels.

REFERENCE LIST

Bishop, R. E., et al. "Transfer of palmitate from phospholipids to lipid A in outer membranes of gram-negative bacteria." *EMBO Journal* 19.19 (2000): 5071-80.

Gervassi, A., et al. "Differential regulation of inflammatory cytokine secretion by human dendritic cells upon *Chlamydia trachomatis* infection." *Infect. Immun.* 72.12 (2004): 7231-39.

Goriely, S., M. F. Neurath, and m. Goldman. "How microorganisms tip the balance between interleukin-12 family members." *Nat. Rev. Immunol.* 8.1 (2008): 81-86.

Guo, L., et al. "lipid A acylation and bacterial resistance against vertebrate antimicrobial peptides." *Cell* 95.2 (1998): 189-98.

Gutcher, I. and B. Becher. "APC-derived cytokines and T cell polarization in autoimmune inflammation." *J. Clin. Invest* 117.5 (2007): 1119-27.

Hoebe, K., et al. "Identification of Lps2 as a key transducer of MyD88-independent TIR signalling." *Nature* 424.6950 (2003): 743-48.

Honda, K., A. Takaoka, and T. Taniguchi. "Type I interferon [corrected] gene induction by the interferon regulatory factor family of transcription factors." *Immunity* 25.3 (2006): 349-60.

Johnson, D. A., et al. "Synthesis and biological evaluation of a new class of vaccine adjuvants: Aminoalkyl glucosaminide 4-phosphates (AGPs)." *Bioorganic and Medicinal Chemistry Letters* 9.15 (1999): 2273-78.

Kawai, T., et al. "Lipopolysaccharide stimulates the MyD88-independent pathway and results in activation of IFN-regulatory factor 3 and the expression of a subset of lipopolysaccharide-inducible genes." *Journal of Immunology* 167.10 (2001): 5887-94.

Kim, H. M., et al. "Crystal structure of the TLR4-MD-2 complex with bound endotoxin antagonist Eritoran." *Cell* 130.5 (2007): 906-17.

Persing, D. H., et al. "Taking toll: lipid A mimetics as adjuvants and immunomodulators." *Trends in Microbiology* 10.10 (2002): S32-S37.

Re, F. and J. L. Strominger. "Toll-like receptor 2 (TLR2) and TLR4 differentially activate human dendritic cells." *Journal of Biological Chemistry* 276.40 (2001): 37692-99.

Rowe, D. C., et al. "The myristoylation of TRIF-related adaptor molecule is essential for Toll-like receptor 4 signal transduction." *Proc. Natl. Acad. Sci. U.S.A* 103.16 (2006): 6299-304.

Stover, A. G., et al. "Structure-activity relationship of synthetic toll-like receptor 4 agonists." *Journal of Biological Chemistry* 279.6 (2004): 4440-49.

——. "Structure-activity relationship of synthetic toll-like receptor 4 agonists." *Journal of Biological Chemistry* 279.6 (2004): 4440-49.

Tailor, P., T. Tamura, and K. Ozato. "IRF family proteins and type I interferon induction in dendritic cells." *Cell Res.* 16.2 (2006): 134-40.

Walsh, C., et al. "Elucidation of the MD-2/TLR4 interface required for signaling by lipid IVa." *Journal of Immunology* 181.2 (2008): 1245-54.

Yamamoto, M., et al. "Role of adaptor TRIF in the MyD88-independent toll-like receptor signaling pathway." *Science* 301.5633 (2003): 640-43.

Yamamoto, M., et al. "TRAM is specifically involved in the Toll-like receptor 4-mediated MyD88-independent signaling pathway." *Nat. Immunol.* 4.11 (2003): 1144-50.

The invention claimed is:

1. A method of improving a lipid A mimetic adjuvant composition's therapeutic index in a human subject, wherein the lipid A mimetic adjuvant composition comprises a first lipid A mimetic that is an aminoalkyl glucosaminide phosphate (AGP) but is not CRX547, the method comprising administering to the human subject a) the first lipid A mimetic, and b) CRX547, wherein the therapeutic index is improved by increasing TRIF-dependent immunity and by lowering MyD88-dependent inflammation induced by the first lipid A mimetic.

* * * * *